US012626804B2

(12) United States Patent
Bose et al.

(10) Patent No.: US 12,626,804 B2
(45) Date of Patent: May 12, 2026

(54) SYSTEM AND METHOD FOR DETERMINING A PERSONALIZED PROBIOTIC THERAPEUTIC REGIMEN

(71) Applicant: Tata Consultancy Services Limited, Mumbai (IN)

(72) Inventors: Tungadri Bose, Pune (IN); Anirban Dutta, Pune (IN); Nishal Kumar Pinna, Pune (IN); Sharmila Shekhar Mande, Pune (IN); Rohan Singh, Pune (IN)

(73) Assignee: Tata Consultancy Services Limited, Mumbai (IN)

( * ) Notice: Subject to any disclaimer, the term of this patent is extended or adjusted under 35 U.S.C. 154(b) by 0 days.

(21) Appl. No.: 18/815,981

(22) Filed: Aug. 27, 2024

(65) Prior Publication Data

US 2025/0104840 A1 Mar. 27, 2025

(30) Foreign Application Priority Data

Sep. 26, 2023 (IN) ............................. 202321064646

(51) Int. Cl.
*G16H 10/40* (2018.01)
*G16B 10/00* (2019.01)
*G16H 20/60* (2018.01)

(52) U.S. Cl.
CPC ............. *G16H 20/60* (2018.01); *G16B 10/00* (2019.02); *G16H 10/40* (2018.01)

(58) Field of Classification Search
None
See application file for complete search history.

(56) References Cited

U.S. PATENT DOCUMENTS

2021/0381024 A1* 12/2021 Farmer .................... C12Q 1/04

FOREIGN PATENT DOCUMENTS

WO WO 2020/086413 A1 4/2020

OTHER PUBLICATIONS

Diener C, Gibbons SM, Resendis-Antonio O. MICOM: Metagenome-Scale Modeling To Infer Metabolic Interactions in the Gut Microbiota. mSystems. Jan. 21, 2020;5(1):e00606-19. doi: 10.1128/mSystems.00606-19. PMID: 31964767; PMCID: PMC6977071. (Year: 2020).*

(Continued)

*Primary Examiner* — Joshua B Blanchette
(74) *Attorney, Agent, or Firm* — Finnegan, Henderson, Farabow, Garrett & Dunner, LLP

(57) ABSTRACT

Existing techniques fail to provide a method to cumulate effects of interactions between groups of gut-associated microbes to predict efficiency of a probiotic organism in an individual. The present disclosure collects a test biological sample from the subject requiring personalization and extracts DNA from test biological sample and information specific to dietary preferences of the subject. Organisms from probiotic organisms dataset are obtained and a plurality of genome scale metabolic models are created for microbes comprised in gut microbiota of subject and obtained probiotic organisms. Metabolic simulations are performed to ascertain monoculture and co-culture growth of every pair of organisms comprised in gut microbiota of subject and obtained probiotic organisms. Sustainability is computed for evaluating capability of each organism to proliferate within gut. Net-effect is computed by quantifying an overall influence of each probiotic organism. An efficacious probiotic organism is selected based on at least one of net-effect and sustainability.

18 Claims, 5 Drawing Sheets

(56) References Cited

OTHER PUBLICATIONS

James D Brunner, Nicholas Chia (2022) Metabolic model-based ecological modeling for probiotic design; arXiv:2210.03198v1 [q-bio. QM] Oct. 6, 2022.*
Hermann-Bank, M.L., Skovgaard, K., Stockmarr, A. et al. The Gut Microbiotassay: a high-throughput qPCR approach combinable with next generation sequencing to study gut microbial diversity. BMC Genomics 14, 788 (2013). https://doi.org/10.1186/1471-2164-14-788 (Year: 2013).*
Bauer et al., "From Network Analysis to Functional Metabolic Modeling of the Human Gut Microbiota," American Society of Microbiology, 3(3) (2018).
Dunphy et al., "Biomedical applications of genome-scale metabolic network reconstructions of human pathogens," Curr Opin Biotechnol., 51:70-79 (2018).
Gibbons et al., "Perspective: Leveraging the Gut Microbiota to Predict Personalized Responses to Dietary, Prebiotic, and Probiotic Interventions," Adv Nutr, 13:1450-1461 (2022).
Jansma et al., "Understanding the host-microbe interactions using metabolic modeling," Microbiome, 9:16 (2021).
Leeming et al., "Effect of Diet on the Gut Microbiota: Rethinking Intervention Duration," Nutrients, 11, (2019).
Sen et al., "Metabolic Modeling of Human Gut Microbiota on a Genome Scale: An Overview," Metabolites, (2019).
Song et al., "Personalized Diets based on the Gut Microbiome as a Target for Health Maintenance: from Current Evidence to Future Possibilities," J. Microbiol. Biotechnol., 32(12) (2022).

* cited by examiner

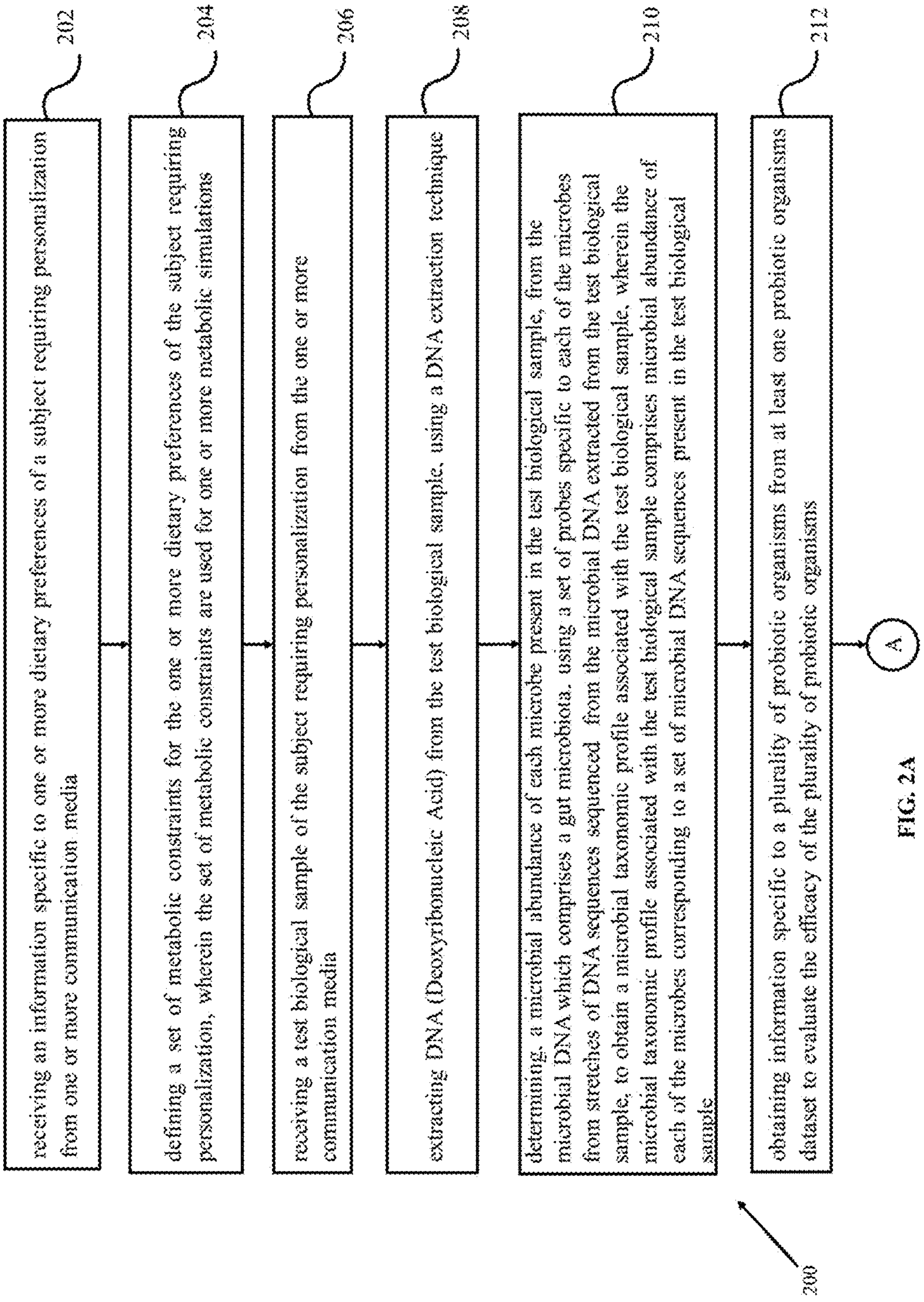

FIG. 2A

202 — receiving an information specific to one or more dietary preferences of a subject requiring personalization from one or more communication media 204 — defining a set of metabolic constraints for the one or more dietary preferences of the subject requiring personalization, wherein the set of metabolic constraints are used for one or more metabolic simulations 206 — receiving a test biological sample of the subject requiring personalization from the one or more communication media 208 — extracting DNA (Deoxyribonucleic Acid) from the test biological sample, using a DNA extraction technique 210 — determining, a microbial abundance of each microbe present in the test biological sample, from the microbial DNA which comprises a gut microbiota, using a set of probes specific to each of the microbes from stretches of DNA sequences sequenced from the microbial DNA extracted from the test biological sample, to obtain a microbial taxonomic profile associated with the test biological sample, wherein the microbial taxonomic profile associated with the test biological sample comprises microbial abundance of each of the microbes corresponding to a set of microbial DNA sequences present in the test biological sample 212 — obtaining information specific to a plurality of probiotic organisms from at least one probiotic organisms dataset to evaluate the efficacy of the plurality of probiotic organisms

A

200

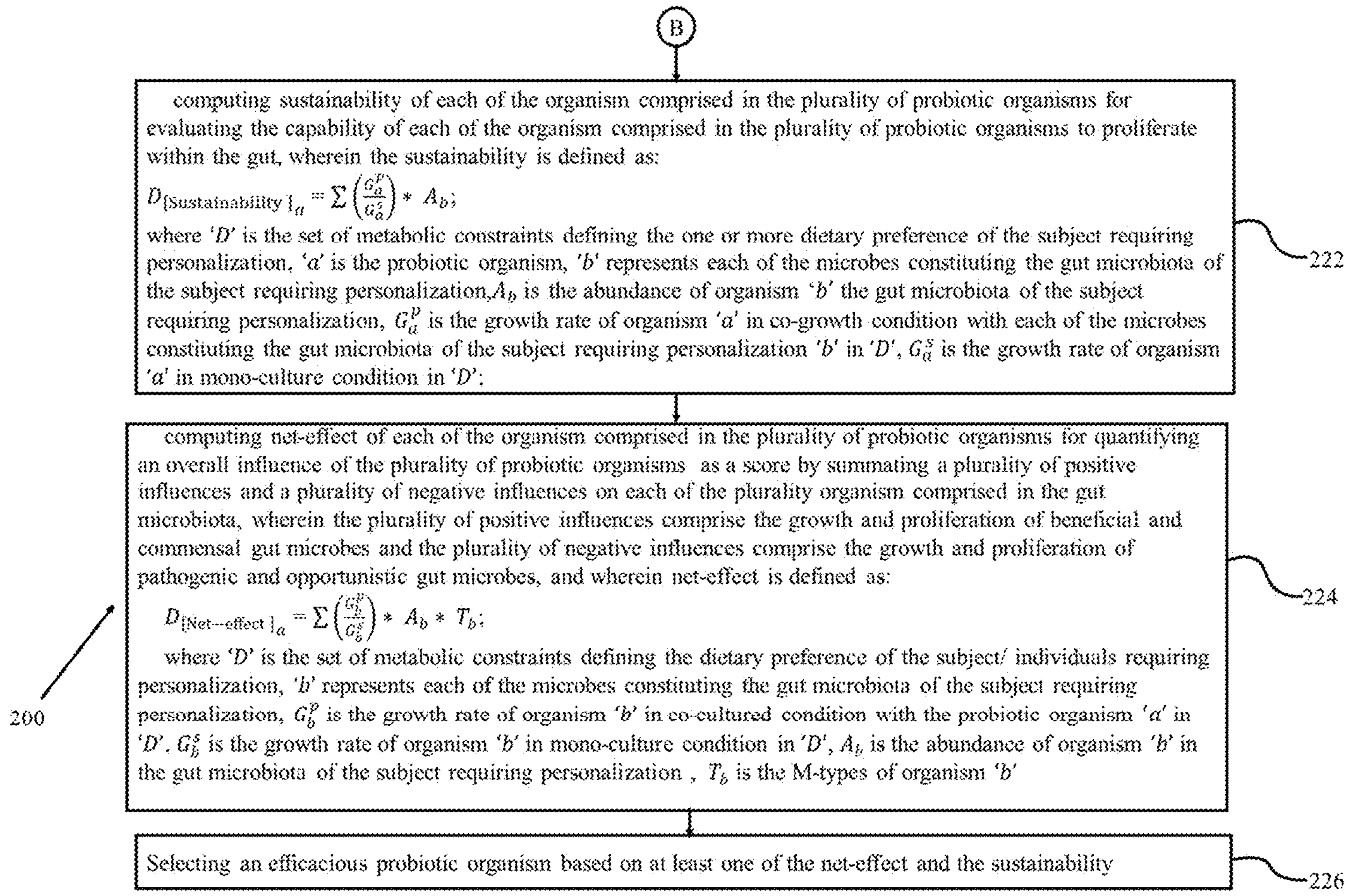

FIG. 2C (B)

computing sustainability of each of the organism comprised in the plurality of probiotic organisms for evaluating the capability of each of the organism comprised in the plurality of probiotic organisms to proliferate within the gut, wherein the sustainability is defined as:

$$D_{[Sustainability]_a} = \sum \left( \frac{G_a^p}{G_a^s} \right) * A_b;$$

where 'D' is the set of metabolic constraints defining the one or more dietary preference of the subject requiring personalization, 'a' is the probiotic organism, 'b' represents each of the microbes constituting the gut microbiota of the subject requiring personalization, $A_b$ is the abundance of organism 'b' the gut microbiota of the subject requiring personalization, $G_a^p$ is the growth rate of organism 'a' in co-growth condition with each of the microbes constituting the gut microbiota of the subject requiring personalization 'b' in 'D', $G_a^s$ is the growth rate of organism 'a' in mono-culture condition in 'D';

— 222 computing net-effect of each of the organism comprised in the plurality of probiotic organisms for quantifying an overall influence of the plurality of probiotic organisms as a score by summating a plurality of positive influences and a plurality of negative influences on each of the plurality organism comprised in the gut microbiota, wherein the plurality of positive influences comprise the growth and proliferation of beneficial and commensal gut microbes and the plurality of negative influences comprise the growth and proliferation of pathogenic and opportunistic gut microbes, and wherein net-effect is defined as:

$$D_{[Net-effect]_a} = \sum \left( \frac{G_b^p}{G_b^s} \right) * A_b * T_b;$$

where 'D' is the set of metabolic constraints defining the dietary preference of the subject/ individuals requiring personalization, 'b' represents each of the microbes constituting the gut microbiota of the subject requiring personalization, $G_b^p$ is the growth rate of organism 'b' in co-cultured condition with the probiotic organism 'a' in 'D', $G_b^s$ is the growth rate of organism 'b' in mono-culture condition in 'D', $A_b$ is the abundance of organism 'b' in the gut microbiota of the subject requiring personalization , $T_b$ is the M-types of organism 'b'

— 224

200

Selecting an efficacious probiotic organism based on at least one of the net-effect and the sustainability

— 226

SYSTEM AND METHOD FOR DETERMINING A PERSONALIZED PROBIOTIC THERAPEUTIC REGIMEN

PRIORITY CLAIM

This U.S. patent application claims priority under 35 U.S.C. § 119 to: Indian Patent Application number 202321064646, filed on Sep. 26, 2023. The entire contents of the aforementioned application are incorporated herein by reference.

TECHNICAL FIELD

The disclosure herein generally relates to the field of monitoring health of an individual, and, more particularly, to a system and method for determining a personalized probiotic therapeutic regimen.

BACKGROUND

The advent of metagenomics has led to significant advances in understanding how the bacterial microbiome is in symbiotic association with different body sites in humans. Gastro-intestinal (GI) tract is the major site of bacterial colonization, and it is well established that taxonomic constitution of gut microbiome influences gut health of the host. A microbiota residing within/on the human body is repeatedly being proven to be a significant modulator of health. While the bacteria harmful to gut represent the pathogens, the commensals represent beneficial gut bacteria.

The human gut microbiota, which comprise of trillions of microbial cells, has been linked to host health status in several recent studies. Given the established role of gut microbiota in digestion, energy harvesting, immunity, etc., this link between the host health status and gut microbiota composition is not surprising. It is, however, important to note that the gut microbiota composition tends to vary even among apparently healthy individuals. In an earlier seminal work introducing the concept of 'enterotypes' in 2011, it was reported that (healthy) humans may be stratified into distinct categories (enterotypes) based on the intestinal microbiota makeup. While the original definition of only three 'enterotype' clusters and any expectation related to distinct boundaries of such clusters may be a generalization, several subsequent studies agree with the basic premise of 'enterotypes' and have shown that individuals of different ethnicities and those residing in different parts of the planet harbour different sets of microbes in their gut. Even, different dietary preferences are known to drive abundance of certain microbes in the gut.

In this context, it may be expected that probiotic interventions on individuals with different gut-microbiota-types will lead to alternate outcomes. Probiotics are primarily bacteria or yeast strains that are used to restore/boost the beneficial functions of the gut microbiota, primarily through metabolic cooperation with the beneficial/commensal inhabitants of the gut or by sensitizing the host immune repertoire. While large scale longitudinal in vivo experiments to investigate the effect of different probiotic interventions among individuals of different ethnicity, dietary preferences, etc. would be costly and might raise ethical concerns, in vitro experiments are also infeasible due to the challenges associated with culturing most gut microbes in the laboratory. Consequently, the effect of probiotics in the context of different gut microbiota compositions and/or diet preferences has remained largely unexplored.

Earlier studies have shown that the use of antibiotics to treat infections often cleanse the beneficial microbes from the gut as a collateral. This increases the chances of a secondary infection by an enteric pathogen or even an opportunistic pathogen. To mitigate this risk, physicians around the world are increasing prescribing probiotics alongside antimicrobial therapies for infections. However, there is a lack of clear guidelines on the choice and usage of probiotics for different clinical conditions.

SUMMARY

Embodiments of the present disclosure present technological improvements as solutions to one or more of the above-mentioned technical problems recognized by the inventors in conventional systems. For example, in one embodiment, a method for determining a personalized probiotic therapeutic regimen is provided. The method includes receiving, via one or more hardware processors, an information specific to one or more dietary preferences of a subject requiring personalization from one or more communication media; defining, via the one or more hardware processors, a set of metabolic constraints for the one or more dietary preferences of the subject requiring personalization, wherein the set of metabolic constraints are used for one or more metabolic simulations; receiving, via the one or more hardware processors, a test biological sample of the subject requiring personalization from the one or more communication media; extracting, via the one or more hardware processors, DNA (Deoxyribonucleic Acid) from the test biological sample, using a DNA extraction technique; determining, via the one or more hardware processors, a microbial abundance of each microbe present in the test biological sample, from the microbial DNA which comprises a gut microbiota, using a set of probes specific to each of the microbes from stretches of DNA sequences sequenced from the microbial DNA extracted from the test biological sample, to obtain a microbial taxonomic profile associated with the test biological sample, wherein the microbial taxonomic profile associated with the test biological sample comprises microbial abundance of each of the microbes corresponding to a set of microbial DNA sequences present in the test biological sample; obtaining, via the one or more hardware processors, an information specific to a plurality of probiotic organisms from at least one probiotic organisms dataset to evaluate the efficacy of the plurality of probiotic organisms; creating, via the one or more hardware processors, a plurality of genome scale metabolic models of each of a plurality of microbes comprised in the gut microbiota of the subject and each of the plurality of probiotic organisms whose efficacy are be evaluated; assigning, via the one or more hardware processors, M-type to the plurality of microbes comprised in the gut microbiota as T=+1 for at least one of beneficial microbes and commensal microbes and T=−1 for at least one of pathogenic microbes and opportunistic microbes; performing, via the one or more hardware processors, the one or more metabolic simulations to ascertain a mono-culture growth of each of the plurality of microbes comprising the gut microbiota and each of the organism comprised in the plurality of probiotic organisms by using the defined set of metabolic constraints for simulating the one or more dietary preferences of the subject; performing, via the one or more hardware processors, the one or more metabolic simulations to ascertain a co-culture growth of every pair of the plurality of microbes comprised in the gut microbiota and each of the organism comprised in the plurality of probiotic organisms by using the defined set of metabolic constraints for simulating the one or more dietary preferences of the subject; computing, via the one or more hardware processors, sustainability of each of the organism comprised in the plurality of probiotic organisms for evaluating the capability of each of the organism comprised in the plurality of probiotic organisms to proliferate within the gut, wherein the sustainability is defined as:

$$D_{[Sustainability]_a} = \sum\left(\frac{G_a^p}{G_a^s}\right) * A_b;$$

where 'D' is the set of metabolic constraints defining the one or more dietary preferences of the subject requiring personalization, 'a' is the probiotic organism, 'b' represents each of the microbes constituting the gut microbiota of the subject requiring personalization, $A_b$ is the abundance of organism 'b' the gut microbiota of the subject requiring personalization, $G_a^p$ is the growth rate of organism 'a' in co-growth condition with each of the microbes constituting the gut microbiota of the subject requiring personalization 'b' in 'D', $G_a^s$ is the growth rate of organism 'a' in mono-culture condition in 'D'; computing, via the one or more hardware processors, net-effect of each of the organism comprised in the plurality of probiotic organisms for quantifying an overall influence of the plurality of probiotic organisms as a score by summating a plurality of positive influences and a plurality of negative influences on each of the microbes comprised in the gut microbiota, wherein the plurality of positive influences comprise the growth and proliferation of at least one of the beneficial microbes and at least one of the commensal microbes and the plurality of negative influences comprises the growth and proliferation of at least one of the pathogenic microbes and at least one of the opportunistic microbes, and wherein the net-effect is defined as:

$$D_{[Net\text{-}effect]_a} = \sum\left(\frac{G_b^p}{G_b^s}\right) * A_b * T_b;$$

where 'D' is the set of metabolic constraints defining the one or more dietary preference of the subject requiring personalization, 'b' represents each of the microbes constituting the gut microbiota of the subject requiring personalization, $G_b^p$ is the growth rate of organism 'b' in co-cultured condition with the probiotic organism 'a' in 'D', $G_b^s$ is the growth rate of organism 'b' in mono-culture condition in 'D', $A_b$ is the abundance of organism 'b' in the gut microbiota of the subject requiring personalization, $T_b$ is the M-types of organism 'b'; and selecting, via the one or more hardware processors, an efficacious probiotic organism based on at least one of the net-effect and the sustainability.

In another aspect, there is provided a system for determining a personalized probiotic therapeutic regimen. The system comprises: a memory storing instructions; one or more communication interfaces; and one or more hardware processors coupled to the memory via the one or more communication interfaces, wherein the one or more hardware processors are configured by the instructions to: receive an information specific to one or more dietary preferences of a subject requiring personalization from one or more communication media. The system further comprises; defining a set of metabolic constraints for the one or more dietary preferences of the subject requiring personalization, wherein the set of metabolic constraints are used as one or more metabolic simulations; receiving a test biological sample of the subject requiring personalization from the one or more communication media; extracting DNA (Deoxyribonucleic Acid) from the test biological sample, using a DNA extraction technique; determining a microbial abundance of each microbe present in the test biological sample, from the microbial DNA which comprises a gut microbiota, using a set of probes specific to each of the microbes from stretches of DNA sequences sequenced from the microbial DNA extracted from the test biological sample, to obtain a microbial taxonomic profile associated with the test biological sample, wherein the microbial taxonomic profile associated with the test biological sample comprises microbial abundance of each of the microbes corresponding to a set of microbial DNA sequences present in the test biological sample; obtaining an information specific to a plurality of probiotic organisms from at least one probiotic organisms dataset to evaluate the efficacy of the plurality of probiotic organisms; creating a plurality of genome scale metabolic models of each of a plurality of microbes comprised in the gut microbiota of the subject and each of the plurality of probiotic organisms whose efficacy are be evaluated; assigning M-type to the plurality of microbes comprised in the gut microbiota as T=+1 for at least one of beneficial microbes and commensal microbes and T=−1 for at least one of pathogenic microbes and opportunistic microbes; performing the one or more metabolic simulations to ascertain a mono-culture growth of each of the plurality of microbes comprising the gut microbiota and each of the organism comprised in the plurality of probiotic organisms by using the defined set of metabolic constraints for simulating the one or more dietary preferences of the subject; performing the one or more metabolic simulations to ascertain a co-culture growth of every pair of the plurality of microbes comprised in the gut microbiota and each of the organism comprised in the plurality of probiotic organisms by using the defined set of metabolic constraints for simulating the one or more dietary preferences of the subject; computing sustainability of each of the organism comprised in the plurality of probiotic organisms for evaluating the capability of each of the organism comprised in the plurality of probiotic organisms to proliferate within the gut, wherein the sustainability is defined as:

$$D_{[Sustainability]_a} = \sum\left(\frac{G_a^p}{G_a^s}\right) * A_b;$$

where 'D' is the set of metabolic constraints defining the one or more dietary preferences of the subject requiring personalization, 'a' is the probiotic organism, 'b' represents each of the microbes constituting the gut microbiota of the subject requiring personalization, $A_b$ is the abundance of organism 'b' the gut microbiota of the subject requiring personalization, $$G_a^p$$

is the growth rate of organism 'a' in co-growth condition with each of the microbes constituting the gut microbiota of the subject requiring personalization 'b' in 'D', $$G_a^s$$

is the growth rate of organism 'a' in mono-culture condition in 'D'; computing net-effect of each of the organism comprised in the plurality of probiotic organisms for quantifying an overall influence of the plurality of probiotic organisms as a score by summating a plurality of positive influences and a plurality of negative influences on each of the microbes comprised in the gut microbiota, wherein the plurality of positive influences comprise the growth and proliferation of at least one of the beneficial microbes and at least one of the commensal microbes and the plurality of negative influences comprises the growth and proliferation of at least one of the pathogenic microbes and at least one of the opportunistic microbes, and wherein the net-effect is defined as:

$$D_{[Net-effect]_a} = \sum\left(\frac{G_b^p}{G_b^s}\right) * A_b * T_b;$$

where 'D' is the set of metabolic constraints defining the one or more dietary preference of the subject requiring personalization, 'b' represents each of the microbes constituting the gut microbiota of the subject requiring personalization, $$G_b^p$$

is the growth rate of organism 'b' in co-cultured condition with the probiotic organism 'a' in 'D', $$G_b^s$$

is the growth rate of organism 'b' in mono-culture condition in 'D', $A_b$ is the abundance of organism 'b' in the gut microbiota of the subject requiring personalization, $T_b$ is the M-types of organism 'b'; and selecting an efficacious probiotic organism based on at least one of the net-effect and the sustainability.

In yet another aspect, there are provided one or more non-transitory machine-readable information storage mediums comprising one or more instructions which when executed by one or more hardware processors cause receiving, via one or more hardware processors, information specific to one or more dietary preferences of a subject requiring personalization from one or more communication media; defining a set of metabolic constraints for the one or more dietary preferences of the subject requiring personalization, wherein the set of metabolic constraints are used as one or more metabolic simulations; receiving a test biological sample of the subject requiring personalization from the one or more communication media; extracting DNA (Deoxyribonucleic Acid) from the test biological sample, using a DNA extraction technique; determining a microbial abundance of each microbe present in the test biological sample, from the microbial DNA which comprises a gut microbiota, using a set of probes specific to each of the microbes from stretches of DNA sequences sequenced from the microbial DNA extracted from the test biological sample, to obtain a microbial taxonomic profile associated with the test biological sample, wherein the microbial taxonomic profile associated with the test biological sample comprises microbial abundance of each of the microbes corresponding to a set of microbial DNA sequences present in the test biological sample; obtaining an information specific to a plurality of probiotic organisms from at least one probiotic organisms dataset to evaluate the efficacy of the plurality of probiotic organisms; creating a plurality of genome scale metabolic models of each of a plurality of microbes comprised in the gut microbiota of the subject and each of the plurality of probiotic organisms whose efficacy are be evaluated; assigning M-type to the plurality of microbes comprised in the gut microbiota as T=+1 for at least one of beneficial microbes and commensal microbes and T=−1 for at least one of pathogenic microbes and opportunistic microbes; performing the one or more metabolic simulations to ascertain a mono-culture growth of each of the plurality of microbes comprising the gut microbiota and each of the organism comprised in the plurality of probiotic organisms by using the defined set of metabolic constraints for simulating the one or more dietary preferences of the subject; performing the one or more metabolic simulations to ascertain a co-culture growth of every pair of the plurality of microbes comprised in the gut microbiota and each of the organism comprised in the plurality of probiotic organisms by using the defined set of metabolic constraints for simulating the one or more dietary preferences of the subject; computing sustainability of each of the organism comprised in the plurality of probiotic organisms for evaluating the capability of each of the organism comprised in the plurality of probiotic organisms to proliferate within the gut, wherein the sustainability is defined as $$D_{[Sustainability]_a} = \sum\left(\frac{G_a^p}{G_a^s}\right) * A_b;$$

where 'D' is the set of metabolic constraints defining the one or more dietary preferences of the subject requiring personalization, 'a' is the probiotic organism, 'b' represents each of the microbes constituting the gut microbiota of the subject requiring personalization, $A_b$ is the abundance of organism 'b' the gut microbiota of the subject requiring personalization, $$G_a^p$$

is the growth rate of organism 'a' in co-growth condition with each of the microbes constituting the gut microbiota of the subject requiring personalization 'b' in 'D', $$G_a^s$$

is the growth rate of organism 'a' in mono-culture condition in 'D'; computing net-effect of each of the organism comprised in the plurality of probiotic organisms for quantifying an overall influence of the plurality of probiotic organisms as a score by summating a plurality of positive influences and a plurality of negative influences on each of the microbes comprised in the gut microbiota, wherein the plurality of positive influences comprise the growth and proliferation of at least one of the beneficial microbes and at least one of the commensal microbes and the plurality of negative influences comprises the growth and proliferation of at least one of the pathogenic microbes and at least one of the opportunistic microbes, and wherein the net-effect is defined as:

$$D_{[Net-effect]_a} = \sum\left(\frac{G_b^p}{G_b^s}\right) * A_b * T_b;$$

where 'D' is the set of metabolic constraints defining the one or more dietary preference of the subject requiring personalization, 'b' represents each of the microbes constituting the gut microbiota of the subject requiring personalization, $$G_b^p$$

is the growth rate of organism 'b' in co-cultured condition with the probiotic organism 'a' in 'D', $$G_b^s$$

is the growth rate of organism 'b' in mono-culture condition in 'D', $A_b$ is the abundance of organism 'b' in the gut microbiota of the subject requiring personalization, $T_b$ is the M-types of organism 'b'; and selecting an efficacious probiotic organism based on at least one of the net-effect and the sustainability.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles:

FIGS. 2A through 2C are flow diagrams illustrating the steps involved in the method for determining a personalized probiotic therapeutic regimen, according to some embodiments of the present disclosure.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Glossary

Microbiota: The collection of micro-organisms, such as, bacteria, archaea, protists, fungi, and virus, that inhabit a particular niche or geographical site.

Microbiome: The collection of genetic material of micro-organisms that reside in a particular geographical niche.

Probiotics: A micro-organism or a collection of micro-organisms introduced into the body for its beneficial qualities.

Therapeutic regimen: A pattern of regulating and integrating into daily living a program(s) for treatment of illness and its sequelae that is sufficient for meeting health-related goals and can be strengthened.

Figure 1:
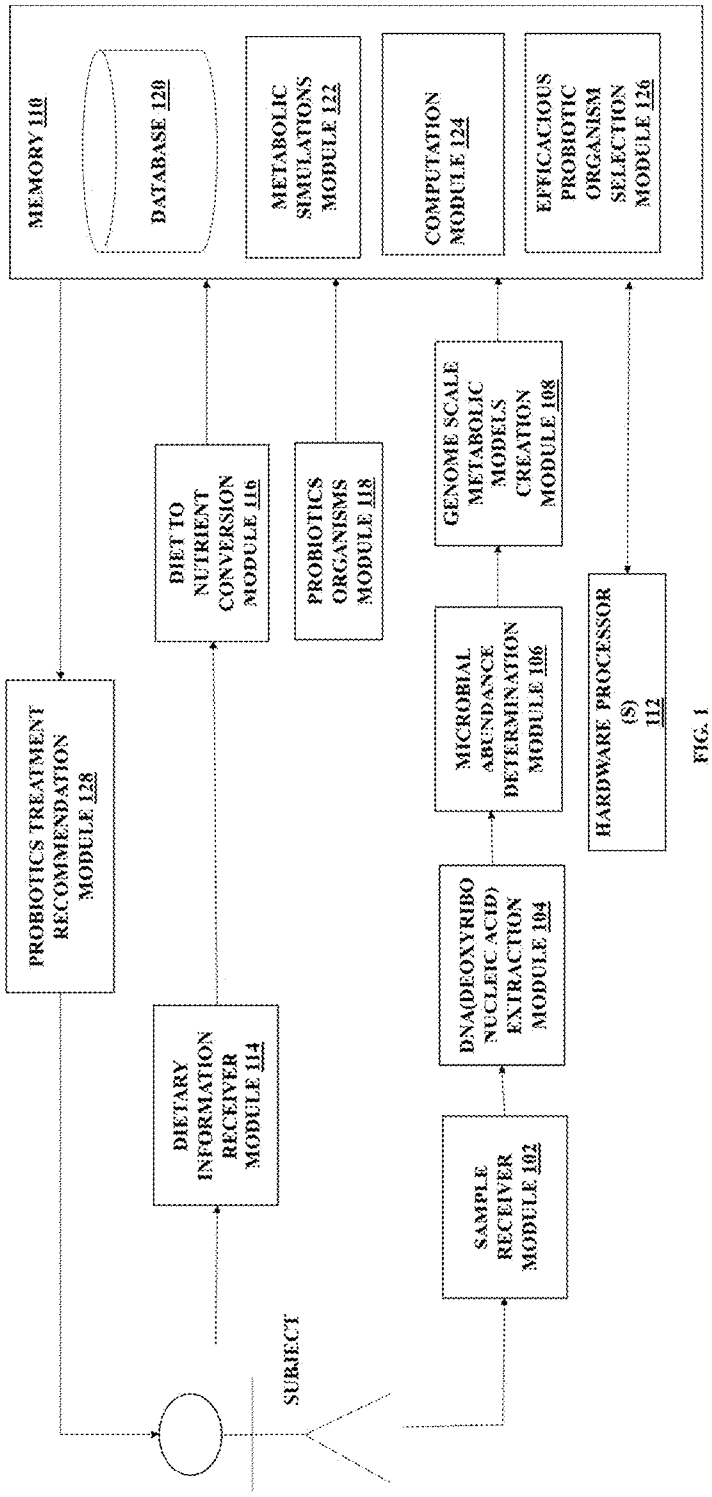
FIG. 1 illustrates a block diagram of a system for determining a personalized probiotic therapeutic regimen in accordance with an embodiment of the disclosure.
Figure 2B:
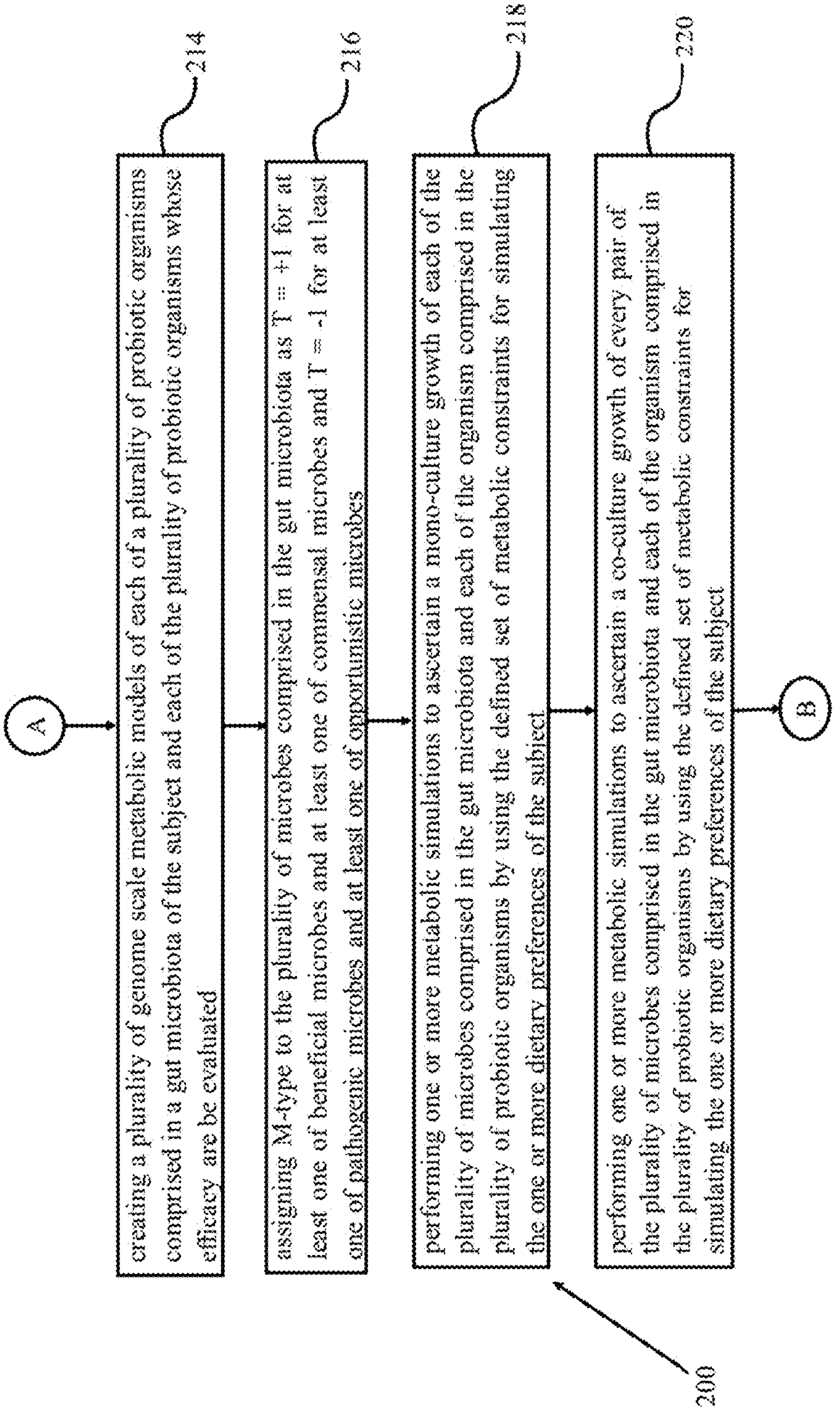
Figure 3:
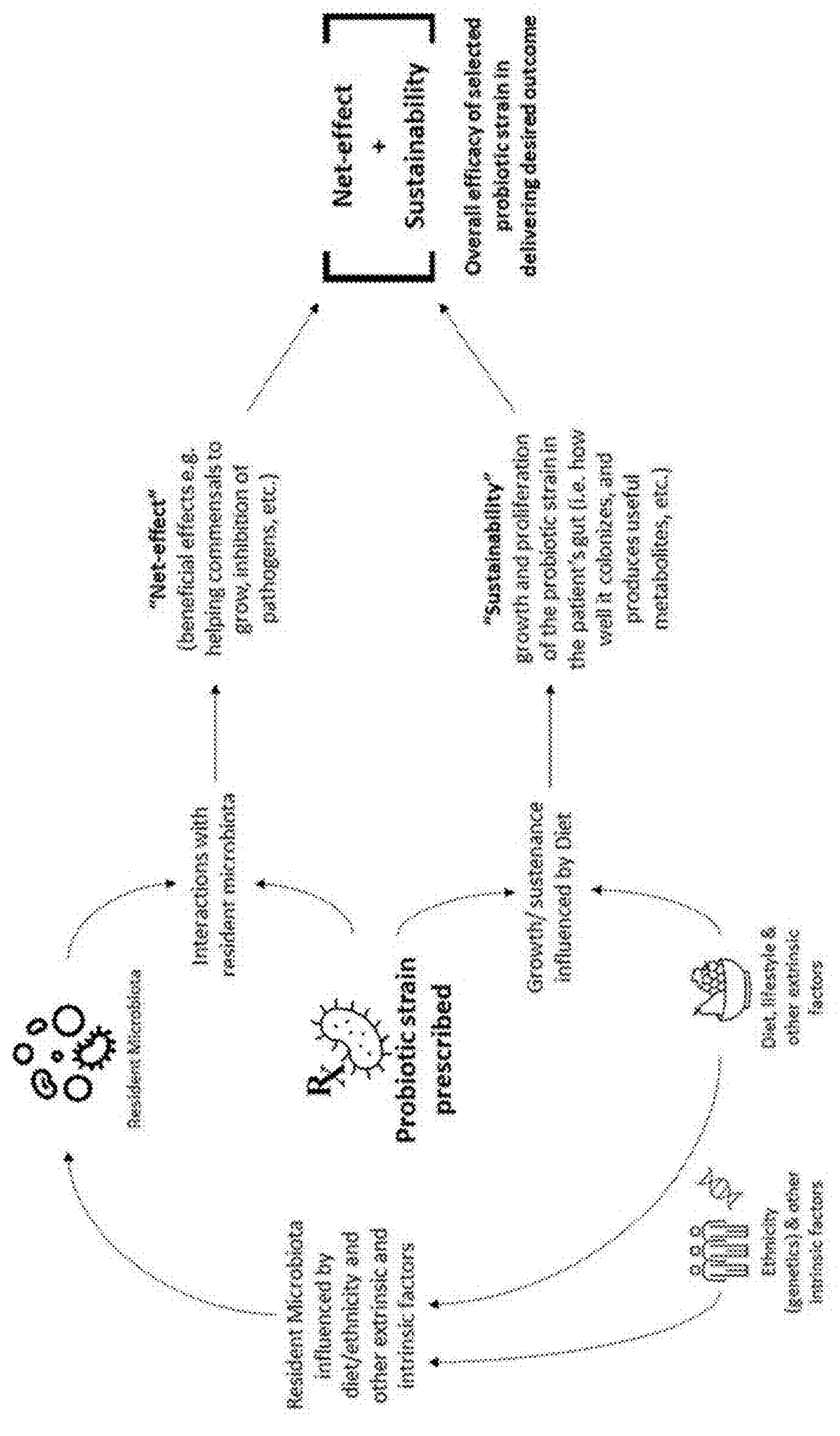
FIG. 3 illustrates a use case example in conjunction with the method for determining a personalized probiotic therapeutic regimen, according to some embodiments of the present disclosure.

Referring now to the drawings, and more particularly to FIG. 1 through FIG. 3, where similar reference characters denote corresponding features consistently throughout the figures, there are shown preferred embodiments and these embodiments are described in the context of the following exemplary system and/or method.

FIG. 1 illustrates a block diagram of a system for determining a personalized probiotic therapeutic regimen in accordance with an embodiment of the disclosure. According to an embodiment of the present disclosure, the system 100 comprises a sample receiver module 102, a DNA (Deoxyribonucleic Acid) extraction module 104, a microbial abundance determination module 106, a genome scale metabolic models creation module 108, a memory 110, one or more hardware processors 112, a dietary information receiver module 114, a diet to nutrient conversion module 116, a probiotics organisms module 118 and a probiotics treatment recommendation module 128 as shown in the block diagram of FIG. 1. In an embodiment, a database 120, a metabolic simulations module 122, a computation module 124 and an efficacious probiotic organism selection module 126 are stored in the memory 110.

In an embodiment, the one or more hardware processors 112 can be implemented as one or more microprocessors, microcomputers, microcontrollers, digital signal processors, central processing units, state machines, logic circuitries, and/or any devices that manipulate signals based on operational instructions. Among other capabilities, the one or more hardware processors 112 is configured to fetch and execute computer-readable instructions stored in the memory 110. In an embodiment, the system 100 can be implemented in a variety of computing systems including laptop computers, notebooks, hand-held devices such as mobile phones, workstations, mainframe computers, servers, a network cloud and the like.

The memory 110 may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and magnetic tapes.

Further, the memory 110 may include a database 120 configured to include information regarding all the available probiotic organisms that can be used for personalizing the therapeutic regimen for a subject. The database 120 is also configured to include information regarding (a) the typical (average) microbiota composition of an ethnic population, (b) the maximum and minimum possible abundance of each of the microbe in the microbiota of an ethnic population based on analysis of publicly available data, (c) the nutritional composition of the typical diet consumed by people from different ethnicities or following different life styles, such as vegetarian diet, western diet, diabetic diet, Mediterranean diet and the like (d) the genome scale metabolic models of microbes already available in the public domain as well as those created for simulation on earlier occasions, (e) The M-types (namely pathogen, commensal or probiotic bacteria) description of each of the microbes corresponding to each of the genome scale metabolic models obtained from public repositories or through literature curation/survey.

The memory 110 may comprise information pertaining to input(s)/output(s) of each step performed by the one or more hardware processors 112 of the system 100 and methods of the present disclosure. In an embodiment, the database 120 may be external (not shown) to the system 100 and coupled to the system 100 via the I/O interfaces (not shown in FIG. 1). In an embodiment, one or more data storage devices or the memory 110 operatively coupled to the one or more hardware processors 112. The system 100 with the one or more hardware processors 112 is configured to execute functions of one or more functional modules of the system 100.

The system 100 supports various connectivity options such as BLUETOOTH®, USB, ZigBee and other cellular services. The network environment enables connection of various components of the system 100 using any communication link including Internet, WAN, MAN, and so on. In an exemplary embodiment, the system 100 is implemented to operate as a stand-alone device. In another embodiment, the system 100 may be implemented to work as a loosely coupled device to a smart computing environment. The components and functionalities of the system 100 are described further in detail.

The present disclosure provides a system and method for determining a personalized probiotic therapeutic regimen based on the monitoring. The present disclosure employs one or more metabolic simulations including a flux balance simulation (FBA) technique to simulate the effect of probiotic interventions on varying gut microbiota compositions and one or more dietary preferences. The present disclosure introduces two metrics, namely 'net-effect' and 'sustainability' to quantify the efficacy (benefits) of probiotic supplementation. In general microbiota refers to the entire habitat of the body, including its microorganisms, genomes, and the surrounding environmental conditions. In an embodiment of the present disclosure the terms "microbiota", "gut microbiota" and "probiotic organisms" are interchangeably used.

According to an embodiment of the disclosure, the sample receiver module 102 of the system 100 is configured to receive test biological sample from the subject requiring personalization, wherein the subject is a human being and wherein the test biological sample can be received from stool of the human subject requiring personalization. The subject can also include other animals as well and hence the present disclosure also has a utility in the veterinary, animal husbandry and fishery/aquaculture segments.

According to an embodiment of the present disclosure, the system 100 further comprises the DNA (Deoxyribonucleic Acid) extraction module 104 that is configured to extract bacterial genomic DNA (Deoxyribonucleic Acid) from the received test biological sample using laboratory standardized protocols. The microbial abundance determination module 106 is configured to determine microbial abundance of each microbe present in the test biological sample, using one of the Next Generation Sequencing (NGS) protocols, to obtain a microbial taxonomic profile associated with the test biological sample, wherein the microbial taxonomic profile associated with the test biological sample comprises microbial abundance of each of the microbes present in the test biological sample. In an alternate implementation, the microbial abundance determination can also be done using multiple DNA characterization techniques including multiplex quantitative Polymerase Chain Reaction (qPCR) technique, nucleic acid hybridization techniques and the like. Additionally, the microbial abundance determination module 106 may also be equipped to quantify the amount of one or more of RNA, proteins or metabolites present in the bacterial cells extracted from the received test biological sample using laboratory standardized protocols, wherein the quantified RNA, proteins or metabolites are used to simulate the effect of probiotic interventions by employing the technique of Flux Balance Analysis (FBA).

According to an embodiment of the present disclosure, the system 100 further comprises the genome scale metabolic models creation module 108 that is configured to create a plurality of genome scale metabolic model of each of a plurality of microbes comprised in the gut microbiota of the subject and each of a plurality of probiotic organisms using genomic information obtained from one of the public databases (e.g., Gene Bank, DDBJ (DNA Data Bank of Japan), etc.). If the genomic data is not available for the organism, the genomic data can be obtained by processing the genomic data generated from Next Generation Sequencing (NGS) through a different pipeline. However, not all forms for genomic data generated using NGS techniques can be used for creating genome scale metabolic model. Only genomic data generated through 'shotgun NGS' protocol is useful. In an alternate implementation, the genome scale metabolic model can be directly sourced from a repository including VMH (Virtual Metabolic Human) Database (1, Virtual Metabolic Human. https://www.vmh.life/. Retrieved 9 May 2022 (known in the art).) and stored in the database 120. Further, the genome scale metabolic model of the plurality of microbes comprised in the gut microbiota of the subject or that of the plurality of probiotic organisms, once created can be stored in the database 120 for future use. The plurality of probiotic organisms is obtained from at least one probiotic organisms dataset (e.g., the set of commercially available probiotic organisms, a list of probiotic organisms surveyed/mentioned in literature, etc.). Table 1 depicts a set of probiotic organisms with known probiotic benefits used in the embodiment of the present disclosure.

TABLE 1

| List of the organisms with known probiotic benefits used in the present disclosure. | |
|---|---|
| Probiotic organisms studied | Metabolic Models used (known in art, Sabina Fijan, 2014) |
| *Bacillus cereus* | *Bacillus_cereus*_G9842 |
| *Bacillus subtilis* | *Bacillus_subtilis*_str_168 |
| *Bifidobacterium adolescentis* | *Bifidobacterium_adolescentis*_ATCC_15703 |
| *Bifidobacterium animalis* | *Bifidobacterium_animalis*_lactis_AD011 |
| *Bifidobacterium bifidum* | *Bifidobacterium_bifidum*_NCIMB_41171 |
| *Bifidobacterium breve* | *Bifidobacterium_breve*_HPH0326 |
| *Bifidobacterium longum* | *Bifidobacterium_longum_longum*_JCM_1217 |
| *Enterococcus durans* | *Enterococcus_durans*_ATCC_6056 |
| *Lactobacillus acidophilus* | *Lactobacillus_acidophilus*_NCFM |
| *Lactobacillus brevis* | *Lactobacillus_brevis*_subsp_*gravesensis*_ATCC_27305 |
| *Lactobacillus casei* | *Lactobacillus_casei*_casei_BL23 |
| *Lactobacillus delbrueckii* | *Lactobacillus_delbrueckii*_subsp_*bulgaricus*_ATCC_11842 |
| *Lactobacillus fermentum* | *Lactobacillus_fermentum*_IFO_3956 |
| *Lactobacillus johnsonii* | *Lactobacillus_johnsonii*_DPC_6026 |
| *Lactobacillus paracasei* | *Lactobacillus_paracasei*_subsp_*paracasei*_ATCC_25302 |
| *Lactobacillus plantarum* | *Lactobacillus_plantarum*_WCFS1 |
| *Lactobacillus reuteri* | *Lactobacillus_reuteri*_MM4_1A |
| *Lactobacillus rhamnosus* | *Lactobacillus_rhamnosus*_GG_ATCC_53103 |
| *Lactococcus lactis* | *Lactococcus_lactis*_subsp_*lactis*_Il1403 |
| *Leuconostoc mesenteroides* | *Leuconostoc_mesenteroides*_subsp_*cremoris*_ATCC_19254 |
| *Pediococcus acidilactici* | *Pediococcus_acidilactici*_7_4 |
| *Streptococcus thermophilus* | *Streptococcus_thermophilus*_LMG_18311 |

In an embodiment of the present disclosure, the dietary information receiver module 114 is configured to receive information specific to the one or more dietary preferences of the subject requiring personalization Different gut-microbiota-types may respond differently to interventions including probiotics, wherein a live biotherapeutic agent (probiotic organism) needs to colonize and proliferate to deliver the desired outcome. The probiotics interaction with the resident microbiota may play a major role in determining the probiotics efficacy. Although the present disclosure has been exemplified using probiotics, in principle, it can also cater to prebiotics, postbiotics and/or a combination therapy of pre, post and probiotics. The era of globalization has also made frequent relocations inevitable often exposing individuals to new diet, lifestyle changes, and the like. This adds another dimension of complexity, given the potential effects of an altered diet on the microbiota, and in turn, on the effect of therapeutic interventions on the microbiota.

In an example embodiment of the present disclosure the one or more dietary preferences of the subject requiring personalization can include oatmeal/cereals with milk and cut-fruits for breakfast (250 grams), diced apples for pre-lunch (50 grams), hand-tossed crust cheese pizza for lunch (250 grams), hamburger with condiments for evening snack (150 grams) and mashed potatoes with assorted vegetables and turkey for dinner (400 grams). The diet to nutrient conversion module 116 is configured to convert the diet of the individual requiring personalization into a list of nutrients and their fluxes/uptake rates at which the nutrients are available for the gut microbes to grow on (i.e., constraints for metabolic simulation). The list of nutrients and the corresponding fluxes/uptake rates are used for the metabolic simulation. Table 2 depicts a nutrient flux file which provides the corresponding flux/uptake rates for the one or more dietary preferences of the subject mentioned above. Information on the nutritional availability for the gut microbes to grow on (fluxes/uptake rates are used for the metabolic simulation) for the common diets, such as vegetarian, European (EU-average), and Mediterranean-style diets can also be obtained from public repositories like the VMH Database—ver 1.03 (known in the art) and stored in the database 120 for future use.

TABLE 2

| Nutrient flux file which provides the corresponding flux/uptake rates. | |
|---|---|
| Nutrient Flux | Uptake rates |
| sucr | 24.65698597560887 |
| glc_D | 62.61243733899363 |
| fru | 58.22734642606764 |
| lcts | 36.88322842915426 |
| malt | 15.469045111474994 |
| gal | 0.9713808984329683 |
| starch1200 | 0.09083352969949335 |
| strch 1 | 9.810931281350921 |
| strch2 | 35.03905640564503 |
| octa | 2.6535664281948415 |
| dca | 4.046557010616227 |
| ddca | 3.898453563246766 |
| ttdca | 13.57300880090428 |
| ptdca | 1.0294561157564368 |
| hdca | 53.121161900130815 |
| hpdca | 0.9853672042330337 |
| ocdca | 22.89313163718258 |
| arach | 0.24075307562054107 |
| docosac | 0.14282533845187934 |
| ttdcea | 1.0561484927030347 |
| hdcea | 3.74111632859156 |
| ocdcea | 66.55808741340483 |
| CE2510 | 0.3812519668401255 |
| lnlc | 41.86267054350257 |
| lnlnca | 2.4583513113790305 |
| arachd | 0.4712335014725222 |
| chsterol | 0.4771714209233849 |
| ca2 | 29.742003093966762 |
| fe2 | 0.19263139045572567 |
| fe3 | 0.19263139045572567 |
| mg2 | 8.557909895083316 |
| pi | 15.58148475765087 |
| k | 54.171153221495565 |
| na1 | 168.3357476478337 |
| zn2 | 0.1580758641786479 |
| cu2 | 0.011771000535 04548 |
| mn2 | 0.03481194134228839 |
| h2o | 39320.510144721586 |
| trp_L | 4.583175827468892 |
| thr_L | 21.104910039691333 |
| ile_L | 23.327989241680257 |
| leu_L | 43.23301535606821 |
| lys_L | 31.821624981741966 |
| met_L | 10.079665548118678 |
| phe_L | 19.520053078562697 |
| tyr_L | 14.106855567544295 |
| val_L | 31.26005686906032 |
| arg_L | 17.52479468794108 |
| his_L | 12.30385692721969 |

TABLE 2-continued

| Nutrient flux file which provides the corresponding flux/uptake rates. | |
| --- | --- |
| Nutrient Flux | Uptake rates |
| ala_D | 15.469755267517607 |
| ala_L | 15.469755267517607 |
| asp_D | 20.73701670089716 |
| asp_L | 20.73701670089716 |
| glu_L | 109.61440939821914 |
| gly | 29.06086062243395 |
| pro_D | 24.598173377167647 |
| pro_L | 24.598173377167647 |
| ser_L | 30.611099163975382 |
| ascb_L | 0.11592302710999897 |
| thm | 0.00952687460477414 |
| ribflv | 0.00804939049680376 |
| nac | 0.12534448798745307 |
| ncam | 0.12532077894216237 |
| pnto_R | 0.01412061752212146 |
| pydam | 0.0028368626662962984 |
| pydx | 0.002871466003038968 |
| pydxn | 0.00283725169614453 |
| adpcbl | 0.0000037636544052356134 |
| retinol | 0.0014697072734102374 |
| caro | 0.001609320348998999 |
| avite1 | 0.009356728404821758 |
| phyQ | 0.00017783617638242392 |
| 5mthf | 0.00009842994154842893 |
| fol | 0.00026482239017960234 |
| thf | 0.00010176735790288656 |
| chol | 1.4716216060546718 |
| but | 1.9805458728868433 |
| lgnc | 0.02040101319591936 |
| doco13ac | 0.04443658410645583 |
| strdnc | 0 |
| tmndnc | 0.0099521269519853 |
| clpnd | 0.03186683184813664 |
| crvnc | 0 |
| etoh | 0 |
| vitd3 | 0.000007799547470255774 |
| CE4843 | 0.01951278526472508 |

In an example embodiment of the present disclosure, a set of metabolic constraints (input parameters), i.e., fluxes/ uptake rates of nutrients to be used for the one or more metabolic simulations are defined based on the one or more dietary preferences of the subject requiring personalization of therapy (as shown in Table 2). The process of conversion of the one or more dietary preferences of the subject to the set of metabolic constraints involve (i) breaking down each of one or more dietary components (e.g., rice/bread, meat/ fish/chicken, green vegetables, fruits, etc.) into their nutritional constituents (e.g. glucose, fructose, glycine, alanine, calcium, iron, vitamin B12, fiber, etc.); and (ii) summing the total quantity of each of the nutrients available to define the maximum availability of that nutrient in the one or more dietary preferences. Further the availability of each of the nutrients can further be modified based on the process of preparing the one or more dietary preferences. For example, cooking on high heat may reduce the amount of nutrients available. Hence, the available nutrients may be multiplied by a 'nutrient loss factor' (ranging between 1 and 0) to accommodate for the loss of nutrients due to the cooking/ food preparation process, wherein food cooked on high heat or extensively processed/preserved has a higher nutrient loss factor, while fresh/raw and minimally cooked/processed food has a low nutrient loss factor.

According to an embodiment of the disclosure, the system 100 further comprises the probiotics organisms module 118 is configured to obtain the plurality of probiotic organisms from at least one probiotic organisms dataset (e.g., the set of commercially available probiotic organisms, a list of probiotic organisms surveyed/mentioned in literature, etc.) as mentioned in one of the earlier sections.

According to an embodiment of the disclosure, the system 100 further comprises the metabolic simulations module 122 which comprises the one or more simulation models (simulating metabolism of organisms in isolation, in paired state, within a community, subjects embracing an alternate diet, etc.) used to simulate the effect of probiotic interventions on varying gut microbiota compositions and the one or more dietary preferences of the subject requiring personalization. In an embodiment of the present disclosure, in-silico metabolic simulation approaches including Flux Balance Analysis (FBA) is utilized to study the effect of probiotic interventions on varying gut microbiota compositions and the one or more dietary preferences of the subject requiring personalization. In an embodiment of the present disclosure, the mono-culture and co-culture growth rates of each of the plurality of microbes constituting the gut microbiota of the subject requiring personalization and each of the plurality of organisms constituting the list of probiotics mentioned in Table 1 are simulated using Flux Balance Analysis (FBA) technique.

In an embodiment of the present disclosure, the computation module 124 is configured to compute net-effect of each of the organism comprised in the plurality of probiotic organisms for quantifying an overall influence of the probiotic organism as a score by summating a plurality of positive influences and a plurality of negative influences on each of the plurality microbes comprised in the gut microbiota. Further the computation module 124 is configured to compute sustainability of each of the plurality of probiotic organisms by measuring the capability of such organism to proliferate within the gut while competing/collaborating for resources with the microbes comprising the gut microbiota.

In an embodiment of the present disclosure, the 'net-effect' reflects the net change in growth rates (weighted in accordance with the abundance of and the beneficial or harmful nature) of the microbes in the gut as a consequence of administering the probiotic (or any other intervention). On the other, the 'sustainability' of an organism (the probiotic organism in this case) has been defined as its capability to proliferate within the gut in presence of the existing microbiota and the given diet. Based on the effects measured using the above metrics, the perspectives presented herein may be further examined and/or exploited for designing personalized probiotic intervention regimes.

In an embodiment of the present disclosure, the efficacious probiotic organism selection module 126 is configured to choose the most efficacious probiotic organism as the best therapeutic candidate based on at least one of the computed net-effect and the sustainability. The probiotics treatment recommendation module 128 is configured to provide recommendation in the form of the probiotics treatment to the individual based on the most efficacious probiotic organism as the best therapeutic candidate chosen as described above, wherein the most efficacious probiotic organism may be chosen as the probiotic organism with the best/highest sustainability as well as the net-effect.

In an alternate example embodiment that has been exemplified in the case study of the present disclosure the one or more dietary preferences of the subject requiring personalization can include vegetarian, European (EU-average), and Mediterranean-style which are obtained from the VMH Database—ver 1.03 (known in the art). While the Mediterranean-style diet is richer in amino acid constituents than the other two diet compositions, the European diet is notable for its larger proportions of several fat constituents. Vegetarian diet comprised of fewer metabolites whose proportions were relatively higher including fructose and sorbitol. Further, when a requirement arises to prescribe probiotics to a certain individual, his/her gut microbiota needs to be profiled as wells as his/her diet needs to be considered. In absence of these information, a generic recommendation can be arrived at considering the typical microbiota make-up of the ethnic group the individual belongs to and considering the typical dietary practices of his/her locality (some of these information can be retrieved and collated from publicly available information). Information regarding this may be obtained from the database 120.

In an example embodiment that has been exemplified in the case study of the present disclosure, the one or more dietary preferences and lifestyle changes can, over time, profoundly change the native gut microbiota composition of an individual. The use case cited in the present disclosure depicts a metabolic simulation design considering microbiota typical to a particular ethnicity/geography consuming (1) usual diet for that region, as well as (2) contexts of alternate dietary regimens pertaining to different regions. The 'representative' microbiota of individuals (gut-microbiota-types) residing in three distinct geographical regions and following local dietary regimes, viz., Indians (for example, from the state of Bhopal) primarily following a vegetarian diet, French following a European diet (EU-average) and Spanish following a Mediterranean-style diet were considered for the case study.

In an example embodiment that has been exemplified in the case study of the present disclosure, the methodology for creating the 'representative' microbiota for individuals representing each of the gut-microbiota-types have been provided here. For each geographical region, the obtained microbial taxas were obtained from previously published studies (data available for download from the Metagenomic Data repository ver 3.2.3—known in the art) and filtered at species level taxonomy. Only those taxas whose percentage normalized abundance values were greater than 0.05 in at least 25% of the samples for that region were considered. Further, those taxas (at species level) for which at least one metabolic model was available (The Virtual Metabolic Human database: integrating human and gut microbiome metabolism with nutrition and disease. Nucleic Acids Res 47: D614-D624.), were considered for the 'representative' microbiota models. For taxas with multiple available models, a representative metabolic model was chosen with the highest growth rate for the diet type consumed by that region's ethnicity. The M-types (namely pathogen, commensal or probiotic bacteria) descriptions of most organisms belonging to the 'representative' microbiota models were already available in the VMH (Virtual Metabolic Human) Database (1, Virtual Metabolic Human. https://www.vmh.life/. Retrieved 9 May 2022). For the rest, a literature survey has been performed to annotate the organisms into different M-type categories which is depicted in Table 3. The M-types of the organisms once available from a public database or through literature curation may be stored in the database 120 for future use. Table 3 depicts details of assigned M-types to unclassified gut organisms based on literature evidence.

TABLE 3

List of assigned M-types to unclassified gut organisms based on literature evidence.

| Organism Name | Model | M-type | References |
|---|---|---|---|
| Alistipes shahii | Alistipes_shahii_ WAL_8301 | Commensal (+1) | pubmed.ncbi.nlm.nih.gov/32582143/ |
| Dialister succinatiphilus | Dialister_ succinatiphilus_ YIT_11850 | Opportunistic pathogen (−1) | pubmed.ncbi.nlm.nih.gov/33748490/ |
| *Haemophilus parainfluenzae* | *Haemophilus_ parainfluenzae_* T3T1 | Pathogen(−1) | pubmed.ncbi.nlm.nih.gov/25209713/ |
| *Enterobacter cloacae* | *Enterobacter_ cloacae*_EcWSU1 | Opportunistic pathogen (−1) | pubmed.ncbi.nlm.nih.gov/26359913/ |
| *Coprococcus catus* | *Coprococcus_ catus*_G D_7 | Probiotic (+1) | pubmed.ncbi.nlm.nih.gov/27988814/ |
| Alistipes indistinctus | Alistipes_ indistinctus_ YIT_12060 | Commensal (+1) | pubmed.ncbi.nlm.nih.gov/32582143/ |
| *Dorea formicigenerans* | *Dorea_ formicigenerans_* ATCC_27755 | Commensal (+1) | pubmed.ncbi.nlm.nih.gov/32272752/ pubmed.ncbi.nlm.nih.gov/31141234/ |
| Alistipes onderdonkii | Alistipes_ onderdonkii_ DSM_19147 | Commensal (+1) | pubmed.ncbi.nlm.nih.gov/32582143/ |
| Paraprevotella clara | Paraprevotella_ clara_YIT_11840 | Opportunistic pathogen (−1) | pubmed.ncbi.nlm.nih.gov/27243236/ |
| *Ruminococcus callidus* | *Ruminococcus_ callidus_* ATCC_2776001 | Commensal (+1) | pubmed.ncbi.nlm.nih.gov/28261015/ pubmed.ncbi.nlm.nih.gov/31108510/ |
| Parasutterella excrementihominis | Parasutterella_ excrementihominis_ YIT_11 859 | Pathogen (−1) | pubmed.ncbi.nlm.nih.gov/32867153/ pubmed.ncbi.nlm.nih.gov/29744928/ |
| *Alistipes finegoldii* | *Alistipes_finegoldii_* D SM_17242 | Commensal (+1) | pubmed.ncbi.nlm.nih.gov/32582143/ |
| *Streptococcus parasanguinis* | *Streptococcus_ parasanguinis_* ATCC_903 | Pathogen (−1) | pubmed.ncbi.nlm.nih.gov/3208745/3 |
| *Clostridium* sp L2 50 | *Clostridium*_sp_ L2_50 | Commensal (+1) | pubmed.ncbi.nlm.nih.gov/15028695/ |

In an embodiment of the present disclosure, selection of the plurality of probiotic organisms with known probiotic benefits was made from an existing study. (Fijan et al. (known in art)). Those plurality of probiotic organisms for which no genome scale metabolic models were available at a species level (from the VMH Database (known in art) were left out of the current study of the present disclosure. Further, the plurality of probiotic organisms, wherein multiple species level models were present, the metabolic model encoding for the largest repertoire of metabolic reactions is chosen.

In an example embodiment that has been exemplified in the case study of the present disclosure, the shotgun metagenomic taxonomic profiles of 173 adults (age≥20 years) belong to three different geographies (akin to three gut-microbiota-types) and following three distinct diet patterns were retrieved from the curated Metagenomic Data repository ver 3.2.3 (known in the art). According to the data submitted by the original researchers to the Metagenomic Data repository ver 3.2.3, at the time of sampling, all the adults considered in the respective studies were healthy and free from any diseases (in the context of original study design). According to the data used in an example embodiment of the present disclosure, *Prevotella copri* (commensal) dominated the gut microbiota of Indian gut-microbiota-type with 47% relative abundance (RA), followed by *Bacteroides plebius* (commensal), *Bacteroides vulgatus* (commensal) and *Eubacterium rectale* (commensal), each with ~3% RA. The Indian also had two microbes that are opportunistic pathogens and a pathogen (*Escherichia coli*). *E. rectale* (commensal) also richly persisted in the French and Spanish cohorts with ~4% RA. *Bacteroides uniformis* (commensal), *B. vulgatus* and *E. rectale* were relatively abundant in all three geographies. *Faecalibacterium prausnitzii* (commensal) was relatively over abundant in the French and Spanish gut-microbiota-types. Ruminococcus bromii (commensal) was the most abundant organism in the French geography (8% RA). Further, the French cohort consisted of four probiotes (two *Bifidobacterium* sp., *Coprococcus catus* and *Streptococcus thermophilus*), and five pathogens (*E. coli, Butyricimonas virosa, Flavonifractor plautii, Parasutterella excrementihominis* and *Streptococcus parasanguinis*). The Spanish cohort consisted of the same four probiotics, as in the French geography, as well as the same pathogens (except *S. parasanguinis*). Available metabolic models corresponding to the microbes comprising the three gut-microbiota-types varied—Spanish cohort had the most representative models by number (61), followed by the French (58) and the Indian cohorts (33). Table 4 depicts that the available metabolic models could represent more than 80% of the microbial abundance for all the three gut-microbiota-types . . .

TABLE 4

Details of gut-microbiota-types and diets analyzed.

| Geographical region | Number of samples (n) | Total microbial species present | Total models available for corresponding species | Sum of mean of abundances of all species present | Sum of representative model abundances | Abundance coverage by representative models |
|---|---|---|---|---|---|---|
| India (Bhopal State) | 49 | 47 | 33 | 86.57 | 77.55 | 89.5% |
| France | 61 | 78 | 58 | 84.12 | 70.17 | 83.4% |
| Spain | 63 | 89 | 61 | 83.95 | 67.89 | 80.0% |

In an embodiment of the present disclosure, the one or more metabolic simulations includes a flux balance simulation using the Flux Balance Analysis (FBA) technique. The Flux Balance Analysis (FBA) allows simulating the metabolic behaviour of an organism under specific environmental conditions (called constraints), such as nutrient availability, stress, etc. In addition to simulating an organism's metabolic behaviour in isolation, the Flux Balance Analysis (FBA) framework can be adapted for studying the concomitant behaviour of multiple organisms and consequently understanding the metabolic interaction patterns among them (A compendium of predicted growths and derived symbiotic relationships between 803 gut microbes in 13 different diets. Current Research in Microbial Sciences 3:100127 (known in art). The metabolic models of the probiotics and the gut microbes, as well as the dietary constraints for the simulation studies were obtained from the VMH Database—ver 1.03 (The Virtual Metabolic Human database: integrating human and gut microbiome metabolism with nutrition and disease. Nucleic Acids Res 47: D614-D624 (known in art)).

In an embodiment of the present disclosure, the effect of gut microbiota and the one or more dietary preferences of the subject is simulated on the outcome of probiotic treatment, using one of 22 different bacteria with known probiotic benefits. The simulation was conducted using gut microbiota makeup of individuals characterized by three distinct dietary preferences and the effect were measured in terms of two metrics, namely, 'net-effect' and 'sustainability'.

In an embodiment of the present disclosure, the genome scale metabolic models representing 800+ organisms were simulated in 13 diets under paired (co-culture) and isolated (mono-culture) conditions and obtained their 'interactome' by measuring the growth of each organism (represented by the corresponding genome scale metabolic model) in the presence of another (A compendium of predicted growths and derived symbiotic relationships between 803 gut microbes in 13 different diets. Singh R, Dutta A, Bose T, Mande S. 2020. Gut Microbe Simulation Data Resource https://doi.org/None, (known in art). The results obtained could further be used in the present disclosure to formulate a metric for probiotic intervention to improve gut microbiota given a set of microbial species derived from an individual for a specific diet. The sustainability of an organism (either as a supplement or any external bacteria) is defined by the capability of such organism to proliferate within the gut. This metric (sustainability) is assumed to demarcate the influence of resident gut microbes on itself. For the set of metabolic constraints D defining a particular dietary regimen, the sustainability of an external microbe a (such as a probiotic organism) is defined as:

$$D_{[Sustainability]_a} = \sum\left(\frac{G_a^p}{G_a^s}\right) * A_b;$$

where b represents each of the microbes constituting the 'representative' microbiota of individuals residing in a distinct geographical region, $A_b$ is the mean abundance of organism b in a population, $G_a^p$ is the growth rate of organism a in paired condition with b in the nutrients available in D, $G_a^s$ is the growth rate of organism a in single condition in the nutrients available in D.

Further, mean values were used in the example for generating population level inferences. However, for individuals walking to clinic requiring personalization, would not encompass computation of 'mean' values (like mean abundance). In such cases, the actual abundance values of each of the microbes constituting their gut microbiota derived from (stool) sample of the patient/subject/individual are to be used. Further, in such a case, the dietary regimen would comprise of the dietary habit of the individual requiring personalization. In an embodiment of the present disclosure the terms "patient", "patient" and "individual" are interchangeably used.

A probiotic supplement could be deduced based on what type and how much of an influence it makes on that set of microbes. A positive influence on a gut community could be demarcated if that probiotic organism (also known as probiote) aids in increasing the growth of other probiotes and/or commensal/helpful organisms and also when probiotes aids in decreasing the growth of harmful/pathogenic bacteria. Conversely, a negative influence is demarcated if the presence/application of that probiote decreases the growth of beneficial/helpful bacteria and/or increases the growth of harmful/pathogenic bacteria. The extent of influence could further be defined by multiplying the abundance value of the gut bacteria to the growth-rate change of the gut microbes in paired (co-culture with the probiote) vs isolated (monoculture) conditions. Therefore, for the set of metabolic constraints D defining a particular dietary regimen, the overall influence could be quantified as a score by summating all positive and negative influences on each model organism present in the gut microbial community. For an (external) probiotic microbe/organisms 'a', net-effect of 'a' was defined as:

$$D_{[Net\text{-}effect]_a} = \sum\left(\frac{G_b^p}{G_b^s}\right) * A_b * T_b;$$

where b represents each of the microbes constituting the 'representative' microbiota of individuals residing in a distinct geographical region $A_b$ is the mean abundance of organism b in a population, $G_b^p$ is the growth rate of organism b in paired condition with the probiotic organism a in the nutrients available in D, $G_b^s$ is the growth rate of organism b in single condition in the nutrients available in D, $T_b$ is the bacteria type e.g., beneficial (+) and harmful (−) of organism b Further, mean values were used in the example for generating population level inferences. However, for individuals walking to clinic requiring personalization, would not encompass computation of 'mean' values (like mean abundance). In such cases, the actual abundance values of each of the microbes constituting their gut microbiota derived from (stool) sample of the patient/subject/individual are to be used. Further, in such a case, the dietary regimen comprises of the dietary habit of the subject requiring personalization.

In an embodiment of the present disclosure, to avoid over-estimating an influence (sustainability or net-effect) due to an extremely large variation in abundance of a microbe comprising the gut microbiota of the subject requiring personalization (with respect to the average abundance of the microbe in the ethnic population/lifestyle/dietary habit to which the subject requiring personalization belong), the, abundance of an organism b observed in the gut microbiota sample of the subject requiring personalization is capped by an abundance factor:

$$A^{factor} = \frac{(3\sigma + A^{max})}{A^{mean}}$$

$A^{max}$=Max Abundance of organism b in population sample (as available in database 120 or from literature survey)

$A^{mean}$=Mean Abundance of organism b in population sample (as available in database 120 or from literature survey)

σ=Standard Deviation of organism b in population sample $$A^{capped} = \min(A_b, A^{factor}), \text{ if } T_b > 0$$

$$\max(A_b, A^{factor}), \text{ if } T_b < 0$$

Where $A^{capped}$ is the capped abundance of microbe b in the gut microbiota and $T_b$ denotes the bacteria type e.g., beneficial (+) and harmful (−) of organism b In an embodiment of the present disclosure, the change in the growth rate of an organism under paired (co-cultured) condition with respect to single (mono-culture) condition is computed via fold change, shown by:

$$\text{Fold change} = G^p - G^s/G^s$$

where $G^p$ is growth of an organism in paired (co-cultured) state with a probiotic organism and $G^s$ is the growth of an organism in single (mono-cultured) state.

In an example embodiment that has been exemplified in the case study of the present disclosure, the net-effect of *Lactobacillus* supplementation was found to be equally beneficial among all the microbiota structures representing each of the three studied gut-microbiota-types viz., Indian, French and Spanish. However, the sustainability demonstrated the better adaptation of *Lactobacillus* strains in vegetarian diet. This was evident from the improvement in *Lactobacillus* sustenance as observed from the simulation involving French and Spanish gut-microbiota-types in vegetarian diet as compared to their native diets (i.e., the European, and Mediterranean-style diets). Further, the sustenance of *Lactobacillus* in the microbiota akin to the Indian gut deteriorated while simulating with European and Spanish diets. The only exception to this observation was *Lactobacillus delbrueckii* subsp. *bulgaricus* ATCC 11842 which demonstrated poor sustenance irrespective of the gut microbiota makeup and dietary regime. *Lactobacillus ruteri* MM4 A1 exhibited the best Sustainability value among all *Lactobacillus* strains in the Mediterranean diet.

In an example embodiment that has been exemplified in the case study of the present disclosure of the present disclosure, similar to the *Lactobacillus* strains, the compatibility as well as the benefits of *Streptococcus thermophilus* was noted to be most profound in the vegetarian diet. In terms of sustainability, *S. thermophilus* LMG 18311 performed better in vegetarian diet, irrespective of the gut-microbiota-type. In contrast, the performance of *Bacillus subtilis* str 168 and *Bacillus cereus* G9842 were seen to be optimal in the Mediterranean diet. Most probiotic species of genus *Bifidobacterium* was observed to grow/sustain relatively well in all the three studied dietary contents (namely vegetarian diet, Mediterranean diet and European diet). Notably, *Bifidobacterium longum* was found to be most compatible with the French gut-microbiota-type. *B. longum* JCM 1217 reported the best net-effect and sustainability values in simulations with the microbiota in the French individuals in all the diets.

In an embodiment, the memory 110 comprises one or more data storage devices operatively coupled to the one or more hardware processors 112 and is configured to store instructions for execution of steps of the method depicted in FIGS. 2A through 2C by the one or more hardware processors 112. FIGS. 2A through 2C are flowcharts illustrating a method 200 for determining a personalized probiotic therapeutic regimen, according to some embodiments of the present disclosure.

The steps of the method 200 of the present disclosure will now be explained with reference to the components or blocks of the system 100 as depicted in FIG. 1 and the steps of flow diagrams as depicted in FIGS. 2A through 2C. Although process steps, method steps, techniques or the like may be described in a sequential order, such processes, methods, and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

FIGS. 2A through 2C are flow diagrams illustrating the steps involved in the method for determining a personalized probiotic therapeutic regimen, according to some embodiments of the present disclosure. Initially at step 202, the one or more hardware processors 112 receive information specific to one or more dietary preferences of a subject/individual requiring personalization from one or more communication media. The one or more communication media can be a mobile phone, laptop, desktop and the like. At step 204, the one or more hardware processors 112 define a set of metabolic constraints (i.e., fluxes/uptake rates at which the nutrients are available for the gut microbes to grow on) for the one or more dietary preferences of the subject requiring personalization, wherein the set of metabolic constraints are used for one or more metabolic simulations. If the one or more dietary preference of the subject requiring personalization is not available, then the set of metabolic constraints are defined based on the common diets of the region/ethnic population to which the subject belongs to. Information regarding the same is obtained from the database 120. In the next step 206, the one or more hardware processors 112 receive a test biological sample from the subject requiring personalization from the one or more communication media. At step 208, the one or more hardware processors 112 extract DNA (Deoxyribonucleic Acid) from the test biological sample using a DNA extraction technique.

At step 210, the one or more hardware processors 112 determine a microbial abundance of each microbe present in the test biological sample, from the microbial DNA, using a set of probes specific to each of the microbes from stretches of DNA sequences sequenced from the microbial DNA extracted from the test biological sample, to obtain a microbial taxonomic profile associated with the test biological sample, wherein the microbial taxonomic profile associated with the test biological sample comprises microbial abundance of each of the microbes corresponding to a set of microbial DNA sequences present in the test biological sample. If the taxonomic profile associated with the test biological sample is not available, then a 'representative' gut microbiota representing the mean microbial abundance of each microbe constituting the gut microbiota of individuals of the ethnic group/lifestyle habits, etc. to which the subject belong to may be used. Information regarding the same can be obtained from the database 120.

At step 212, the one or more hardware processors 112 obtain an information specific to a plurality of probiotic organisms from at least one probiotic organisms dataset to evaluate the efficacy of the plurality of probiotic organisms. If probiotic organisms' dataset is not provided, the list of probiotic organisms stored in the database 120 is used. At step 214, create a plurality of genome scale metabolic models (networks) of each of a plurality of microbes comprised in a gut microbiota of the subject and each of the plurality of probiotic organisms whose efficacy are to be evaluated. The genome scale metabolic models of microbes comprising the gut microbiota and the plurality of probiotic organisms, if already available in the database 120 is used. At step 216, the one or more hardware processors 112 assigns M-types (namely pathogen, commensal or probiotic bacteria) the plurality of microbes comprised in the gut microbiota as T=+1 for at least one of beneficial microbes and at least one of commensal microbes and T=−1 for at least one of pathogenic microbes and at least one of opportunistic microbes. Information on M-type of the microbes constituting the gut microbiota of the subject requiring personalization is obtained from at least one of database 120, a public repository (like VMH) and literature survey.

At step 218 of the method 200, the one or more hardware processors 112 perform one or more metabolic simulations to ascertain a mono-culture growth of each of the plurality of microbes comprising the gut microbiota and each of the organism comprised in the plurality of probiotic organisms by using the defined set of metabolic constraints for simulating the one or more dietary preferences of the subject. At step 220 of the method 200, the one or more hardware processors 112 perform one or more metabolic simulations to ascertain a co-culture growth of every pair of the plurality of microbes comprised in the gut microbiota and each of the organism comprising the plurality of probiotic organisms by using the defined set of metabolic constraints for simulating the one or more dietary preferences of the subject.

At step 222 of the method 200, the one or more hardware processors 112 compute sustainability of each of the organism comprised in the plurality of probiotic organisms for evaluating the capability of each of the organism comprised in the plurality of probiotic organisms to proliferate within the gut, wherein the sustainability is defined as (222):

$$D_{[Sustainability]_a} = \sum\left(\frac{G_a^p}{G_a^s}\right) * A_b;$$

where 'D' is the set of metabolic constraints defining the dietary preference of the subject requiring personalization, 'a' is an external/probiotic organism/microbe, 'b' represents each of the microbes constituting the gut microbiota of the subject/individuals requiring personalization, $A_b$ is the abundance of organism 'b' in the gut microbiota of the subject requiring personalization, $G_a^p$ is the growth rate of organism 'a' in co-growth condition with the resident gut microbe 'b' in 'D', $G_a^s$ is the growth rate of organism 'a' in mono-culture condition in 'D'.

At step 224 of the method 200, the one or more hardware processors 112 compute net-effect of each of the organism comprised in the plurality of probiotic organisms for quantifying an overall influence of the plurality of probiotic organisms as a score by summating a plurality of positive influences and a plurality of negative influences on each of the microbes comprised in the gut microbiota, wherein the plurality of positive influences comprise the growth and proliferation of at least one of the beneficial microbes and at least one of the commensal microbes and the plurality of negative influences comprise the growth and proliferation of at least one of the pathogenic microbes and at least one of the opportunistic microbes, and wherein net-effect is defined as:

$$D_{[Net\text{-}effect]_a} = \sum\left(\frac{G_b^p}{G_b^s}\right) * A_b * T_b;$$

where, 'D' is the set of metabolic constraints defining the dietary preference of the subject/individuals requiring personalization, 'b' represents each of the microbes constituting the gut microbiota of the subject/individuals requiring personalization, $G_b^p$ is the growth rate of organism 'b' in co-cultured (paired) condition with the probiotic organism 'a' in 'D', $G_b^s$ is the growth rate of organism 'b' in monoculture (single) condition in 'D', $A_b$ is the abundance of organism 'b' in the gut microbiota of the subject/individual requiring personalization, $T_b$ is the M-types of organism 'b' [+1 for beneficial/commensal) and −1 for harmful/pathogenic].

At step 226 of the method 200, the one or more hardware processors 112 select an efficacious probiotic organism based on at least one of the net-effect and the sustainability. The most efficacious probiotic organism is chosen as the probiotic organism with the best/highest sustainability as well as the net-effect. The most efficacious probiotic organism with the best/highest sustainability as well as the net-effect is able to deliver optimal therapeutic outcome, i.e., benefits expected from the probiotic intervention. Further, the dosage requirement for the probiotic organism is the least.

FIG. 3 illustrates a use case example in conjunction with the method for determining a personalized probiotic therapeutic regimen, according to some embodiments of the present disclosure. The effect of gut microbiota and the one or more dietary preferences on the outcome of probiotic treatment is illustrated in FIG. 3. The composition of the gut microbiota is influenced by several intrinsic and extrinsic factors including ethnicity and the one or more dietary preferences. In order to impart the expected benefits, a probiotic organism should be able to sustain itself on the nutrients available from the diet consumed by the host. Further, the probiotic organism must interact with other resident microbes in the gut, such that the probiotic organism could promote the growth of beneficial microbes while inhibiting the growth of harmful pathogens.

In a scenario, wherein no probiotic organisms can be identified (from the list of available probiotic organisms) with both the best/highest sustainability as well as net-effect, then a probiotic with the best/highest sustainability and moderately high net-effect may be chosen. Administration of such a probiotic would deliver descent results in terms of the expected therapeutic benefits but the frequent of administration/dosage required would be the least of all available options. Alternatively, a probiotic with the best/highest net-effect and a moderately high sustainability may be chosen. In this case, the effect of the intervention will be most optimal of all the available probiotic therapy options but may require more frequent/higher dosage.

The present disclosure helps understanding (e.g., (e.g., say users) if the diet impacts the interaction between the probiotic and the enteric pathogen. The probiotics used in the present disclosure were co-cultured in silico with the most prominent enteric (bacterial) pathogens (2021. Enteric Diseases Epidemiology Branch|DFWED|NCEZID|CDC. https://www.cdc.gov/ncezid/dfwed/edeb/index.html. Retrieved 9 May 2022.) under three dietary conditions. It was observed that, in most cases, interaction between the probiote and the pathogen, as inferred from the change in growth rate of the pathogen, was seen to vary with diet. However, the magnitude of the change in growth rates in such cases were found to be rather small. In an example embodiment that has been exemplified in the case study of the present disclosure, except for *Camphylobacter coli* JV20 and *Camphylobacter jejuni jejuni*, the growth rate of the enteric pathogen was found to decrease marginally in the presence of the probiotic. Irrespective of the dietary regime, *Bacillus* strains (*B. cereus* G9842 and *B. subtilis* str 168) were found to be beneficial against *Clostridium perfringens, Listeria monocytogenes, Staphylococcus aureus* (Staph) and *Clostridium botulinum*. Probiotics which were found to be extremely efficient against *C. perfringens* infection were *Bifidobacterium* based probiotics, *Leuconostoc mesenteroides* subsp *cremoris* ATCC 19254, *Pediococcus acidilactici* 7_4 and *Streptococcus thermophilus LMG* 18311. Other probiotics which seemed to be potent remedies for various infections include, *Lactococcus lactis* subsp *lactis* 111403 against *L. mesenteroides, C. botulinum* and *Salmonella* infections; *Bifidobacterium adolescentis* ATCC 15703 and *B. longum* JCM 1217 against *Escherichia coli* infection. A few diet-specific trends were also evident. For example, in Staph infection, the efficacy of probiotes seemed to be considerably influenced by the one or more dietary preferences. Similarly, the beneficial effect of *Bifidobacterium breve* HPH0326 in *Vibrio* infection was most prominent in European diet.

The use of probiotics may be grouped into two major categories: (a) the traditional use of probiotics as agents to impart beneficial functions to improve our gut health; and (b) a more recent advancement of substituting or supplementing antimicrobial therapy. Overuse of antimicrobials not only increase the risk of antimicrobial resistance, but also wipes out the beneficial microbes in the gut. Since microbes comprising the gut microbiota have been linked to health and well-being, loss of beneficial microbes often leads to loss of essential physiological functions. Administering probiotics have been shown to not only help in mitigating infections, but also promote beneficial functions in our body. Results of the simulation studies presented herein provides evidence that personalizing the choice of probiotic could enhance the benefits. Further, this choice of probiotics should be governed by at least the nature of the gut microbiota makeup and the dietary preference. Other factors such as, the lifestyle of an individual, underlying diseases, consumption of functional foods (prebiotics), etc., are also expected to influence the impact of probiotics and can be further probed through both in silico as well as clinical studies. Based on findings obtained by simulating the effect of probiotic interventions on varying gut microbiota compositions and the one or more dietary preferences of the subject requiring personalization, the present disclosure hypothesize that the benefits of probiotic consumption can be maximized if the choice of the probiotic organism and/or the dosage/duration of the therapy could be personalized.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein provide system and method for determining a personalized probiotic therapeutic regimen. The embodiment of present disclosure herein addresses unresolved problem of determining the best possible probiotic intervention by considering the one or more dietary preferences and the gut microbiota makeup of the subject. In an embodiment of the present disclosure, the effect of gut microbiota and the one or more dietary preferences of the subject are simulated, and the effect were measured in terms of two newly defined metrics, namely 'net-effect' and 'sustainability. The embodiment further enables to select an efficacious probiotic organism based on at least one of net-effect and sustainability.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A method, comprising:

receiving, via one or more hardware processors, an information specific to one or more dietary preferences of a subject requiring personalization from one or more communication media;

defining, via the one or more hardware processors, a set of metabolic constraints for the one or more dietary preferences of the subject requiring personalization, wherein the set of metabolic constraints are used for one or more metabolic simulations;

receiving, via the one or more hardware processors, a test biological sample of the subject requiring personalization from the one or more communication media;

extracting, via the one or more hardware processors, DNA (Deoxyribonucleic Acid) from the test biological sample, using a DNA extraction technique;

determining, via the one or more hardware processors, a microbial abundance of each microbe present in the test biological sample, from the microbial DNA which comprises a gut microbiota, using a set of probes specific to each of the microbes from stretches of DNA sequences sequenced from the microbial DNA extracted from the test biological sample, to obtain a microbial taxonomic profile associated with the test biological sample, wherein the microbial taxonomic profile associated with the test biological sample comprises microbial abundance of each of the microbes corresponding to a set of microbial DNA sequences present in the test biological sample;

obtaining, via the one or more hardware processors, an information specific to a plurality of probiotic organisms from at least one probiotic organisms dataset to evaluate the efficacy of the plurality of probiotic organisms;

creating, via the one or more hardware processors, a plurality of genome scale metabolic models of each of a plurality of microbes comprised in the gut microbiota of the subject and each of the plurality of probiotic organisms whose efficacy are be evaluated;

assigning, via the one or more hardware processors, M-type to the plurality of microbes comprised in the gut microbiota as T=+1 for at least one of beneficial microbes and commensal microbes and T=−1 for at least one of pathogenic microbes and opportunistic microbes;

performing, via the one or more hardware processors, the one or more metabolic simulations to ascertain a mono-culture growth of each of the plurality of microbes comprising the gut microbiota and each of the organism comprised in the plurality of probiotic organisms by using the defined set of metabolic constraints for simulating the one or more dietary preferences of the subject;

performing, via the one or more hardware processors, the one or more metabolic simulations to ascertain a co-culture growth of every pair of the plurality of microbes comprised in the gut microbiota and each of the organism comprised in the plurality of probiotic organisms by using the defined set of metabolic constraints for simulating the one or more dietary preferences of the subject, wherein the one or more metabolic simulations include in-silico metabolic simulations including a flux balance simulation for simulating metabolic behaviour of an organism under the set of metabolic constraints and simulating an effect of probiotic interventions on a plurality of gut microbiota compositions and the one or more dietary preferences of the subject;

computing, via the one or more hardware processors, sustainability of each of the organism comprised in the plurality of probiotic organisms for evaluating the capability of each of the organism comprised in the plurality of probiotic organisms to proliferate within the gut, wherein the sustainability is defined as:

$$D_{[Sustainability]_a} = \sum\left(\frac{G_a^p}{G_a^s}\right) * A_b;$$

where 'D' is the set of metabolic constraints defining the one or more dietary preferences of the subject requiring personalization, 'a' is the probiotic organism, 'b' represents each of the microbes constituting the gut microbiota of the subject requiring personalization, $A_b$ is the abundance of organism 'b' the gut microbiota of the subject requiring personalization, $$G_a^p$$

is the growth rate of organism 'a' in co-growth condition with each of the microbes constituting the gut microbiota of the subject requiring personalization 'b' in 'D', $$G_a^s$$

is the growth rate of organism 'a' in mono-culture condition in 'D';

computing, via the one or more hardware processors, net-effect of each of the organism comprised in the plurality of probiotic organisms for quantifying an overall influence of the plurality of probiotic organisms as a score by summating a plurality of positive influences and a plurality of negative influences on each of the microbes comprised in the gut microbiota, wherein the plurality of positive influences comprise the growth and proliferation of at least one of the beneficial microbes and at least one of the commensal microbes and the plurality of negative influences comprises the growth and proliferation of at least one of the pathogenic microbes and at least one of the opportunistic microbes, wherein the net-effect reflects a net change in growth rates of the plurality of microbes in the gut microbiota as a consequence of administering a probiotic, and wherein the net-effect is defined as:

$$D_{[Net-effect]_a} = \sum\left(\frac{G_b^p}{G_b^s}\right) * A_b * T_b;$$

where 'D' is the set of metabolic constraints defining the one or more dietary preference of the subject requiring personalization, 'b' represents each of the microbes constituting the gut microbiota of the subject requiring personalization, $$G_b^p$$

is the growth rate of organism 'b' in co-cultured condition with the probiotic organism 'a' in 'D', $$G_b^s$$

is the growth rate of organism 'b' in mono-culture condition in 'D', $A_b$ is the abundance of organism 'b' in the gut microbiota of the subject requiring personalization, $T_b$ is the M-types of organism 'b', wherein the abundance of the organism 'b' in the gut microbiota of the subject requiring personalization is capped by an abundance factor to avoid over-estimating an influence including the sustainability or the net-effect due to large variation in the abundance of the microbe comprising the gut microbiota of the subject requiring personalization;

selecting, via the one or more hardware processors, an efficacious probiotic organism based on at least one of the net-effect and the sustainability;

designing a personalized probiotic intervention regimen in the form of a probiotics treatment to the subject based on the selected efficacious probiotic organism; and administering the efficacious probiotic organism to the subject to improve the gut microbiota, wherein a dosage requirement for the efficacious probiotic organism is least when the efficacious probiotic organism is selected with a highest sustainability and the net-effect to deliver optimal therapeutic outcome, wherein when a probiotic organism with both the highest sustainability and the net-effect is not identified, then a probiotic organism with the highest sustainability and moderately high net-effect is selected and administration or the dosage requirement of the probiotic organism is the least of all available probiotic therapy options, wherein when the probiotic organism with a highest net-effect and a moderately high sustainability is selected, then the effect of the probiotic intervention is optimal of all the available probiotic therapy options, and the dosage requirement of the probiotic organism is more frequent or higher dosage, and wherein the method is implemented for the probiotics treatment to the subject requiring personalization based on the efficacious probiotic organism to improve the gut microbiota.

2. The processor implemented method of claim 1, wherein defining the set of metabolic constraints includes (a) identifying and quantifying one or more nutrients constituting the one or more dietary preferences of the subject requiring personalization, and (b) converting the one or more quantified nutrients into the set of metabolic constraints, and wherein the set of metabolic constraints is defined based on the common diets of at least one of a region and an ethnic population to which the subject belongs to, if the one or more dietary preferences of the subject requiring personalization is not available and the information regarding the one or more dietary preferences of the subject is obtained from the database.

3. The processor implemented method of claim 1, wherein the step of determining the microbial abundance comprises determining the microbial abundance of a predefined set of microbes using multiple DNA characterization techniques including Next Generation Sequencing protocols (NGS), a multiplex quantitative Polymerase Chain Reaction (qPCR) technique, nucleic acid hybridization techniques and the like, and wherein the microbial abundance of each microbe constituting the gut microbiota of the subject is defined as at least one of the mean microbial abundance of each microbe constituting the gut microbiota of an ethnic group and one or more lifestyle habits to which the subject belongs to, using information from the database, if the taxonomic profile associated with the test biological sample is not available.

4. The processor implemented method of claim 1, wherein the probiotic organisms including *Bacillus* strains are beneficial against *Clostridium perfringens, Listeria monocytogenes, Staphylococcus aureus* and *Clostridium botulinum* infections, wherein the probiotic organisms including *Bifidobacterium* based probiotics, *Leuconostoc mesenteroides* subsp *cremoris* ATCC 19254, *Pediococcus acidilactici* 7 4 and *Streptococcus thermophilus* LMG 18311 are efficient against *Clostridium perfringens* infection, wherein the probiotic organisms including *Lactococcus lactis* subsp *lactis* 111403 against *L. mesenteroides, C botulinum* and *Salmonella* infections and *Bifidobacterium adolescentis* ATCC 15703 and *B. longum* JCM 1217 against *Escherichia coli* infection, wherein the abundance factor is represented as $$A^{factor} = \frac{(3\sigma + A^{max})}{A^{mean}}$$

$A^{max}$=max abundance of the organism b in a population sample, $A^{mean}$=mean abundance of the organism b in the population sample, $\sigma$=standard deviation of the organism b in the population sample $$A^{capped} = \min(A_b, A^{factor}), \text{ if } T_b > 0$$

$$\max(A_b, A^{factor}), \text{ if } T_b < 0$$

where $A^{capped}$ is the capped abundance of microbe b in the gut microbiota and $T_b$ denotes a bacteria type including beneficial and harmful of organism b.

5. The processor implemented method of claim 1, wherein a list of probiotic organisms stored in the database is used, if at least one probiotic organisms dataset is not available.

6. The processor implemented method of claim 1, wherein the genome scale metabolic models of microbes comprising the gut microbiota and the plurality of probiotic organisms available in the database is used.

7. The processor implemented method of claim 1, wherein the information regarding M-type of the microbes constituting the gut microbiota of the subject requiring personalization is obtained from at least one of database, a public repository, and a literature survey.

8. A system comprising:

a memory storing instructions; and one or more hardware processors, wherein the one or more hardware processors are configured by the instructions to:

receive an information specific to one or more dietary preferences of a subject requiring personalization from one or more communication media;

define a set of metabolic constraints for the one or more dietary preferences of the subject requiring personalization, wherein the set of metabolic constraints are used for one or more metabolic simulations;

receive a test biological sample of the subject requiring personalization from the one or more communication media;

extract DNA (Deoxyribonucleic Acid) from the test biological sample, using a DNA extraction technique;

determine a microbial abundance of each microbe present in the test biological sample, from the microbial DNA which comprises the gut microbiota, using a set of probes specific to each of the microbes from stretches of DNA sequences sequenced from the microbial DNA extracted from the test biological sample, to obtain a microbial taxonomic profile associated with the test biological sample, wherein the microbial taxonomic profile associated with the test biological sample comprises microbial abundance of each of the microbes corresponding to a set of microbial DNA sequences present in the test biological sample;

obtain an information specific to a plurality of probiotic organisms from at least one probiotic organisms dataset to evaluate the efficacy of the plurality of probiotic organisms;

create a plurality of genome scale metabolic models of each of a plurality of microbes comprised in the gut microbiota of the subject and each of the plurality of probiotic organisms whose efficacy are be evaluated;

assign M-type to the plurality of microbes comprised in the gut microbiota as T=+1 for at least one of beneficial microbes and commensal microbes and T=−1 for at least one of pathogenic microbes and opportunistic microbes;

perform the one or more metabolic simulations to ascertain a mono-culture growth of each of the plurality of microbes comprising the gut microbiota and each of the organism comprised in the plurality of probiotic organisms by using the defined set of metabolic constraints for simulating the one or more dietary preferences of the subject;

perform the one or more metabolic simulations to ascertain a co-culture growth of every pair of the microbes comprised in the gut microbiota and each of the organism comprised in the plurality of probiotic organisms by using the defined set of metabolic constraints for simulating the one or more dietary preferences of the subject, wherein the one or more metabolic simulations include in-silico metabolic simulations including a flux balance simulation for simulating metabolic behaviour of an organism under the set of metabolic constraints and simulating an effect of probiotic interventions on a plurality of gut microbiota compositions and the one or more dietary preferences of the subject;

compute sustainability of each of the organism comprised in the plurality of probiotic organisms for evaluating the capability of each of the organism comprised in the plurality of probiotic organisms to proliferate within the gut, wherein the sustainability is defined as:

$$D_{[Sustainability]_a} = \sum\left(\frac{G_a^p}{G_a^s}\right) * A_b;$$

where 'D' is the set of metabolic constraints defining the one or more dietary preferences of the subject requiring personalization, 'a' is the probiotic organism, 'b' represents each of the microbes constituting the gut microbiota of the subject requiring personalization, $A_b$ is the abundance of organism 'b' the gut microbiota of the subject requiring personalization, $$G_a^p$$

is the growth rate of organism 'a' in co-growth condition with each of the microbes constituting the gut microbiota of the subject requiring personalization 'b' in 'D', $$G_a^s$$

is the growth rate of organism 'a' in mono-culture condition in 'D';

compute net-effect of each of the organism comprised in the plurality of probiotic organisms for quantifying an overall influence of the plurality of probiotic organisms as a score by summating a plurality of positive influences and a plurality of negative influences on each of the microbes comprised in the gut microbiota, wherein the plurality of positive influences comprise the growth and proliferation of at least one of the beneficial microbes and at least one of the commensal microbes and the plurality of negative influences comprise the growth and proliferation of at least one of the pathogenic microbes and at least one of the opportunistic microbes, wherein the net-effect reflects a net change in growth rates of the plurality of microbes in the gut microbiota as a consequence of administering a probiotic, and wherein the net-effect is defined as:

$$D_{[Net-effect]_a} = \sum\left(\frac{G_b^p}{G_b^s}\right) * A_b * T_b;$$

where 'D' is the set of metabolic constraints defining the one or more dietary preference of the subject requiring personalization, 'b' represents each of the microbes constituting the gut microbiota of the subject requiring personalization, $$G_b^p$$

is the growth rate of organism 'b' in co-cultured condition with the probiotic organism 'a' in 'D', $$G_b^s$$

is the growth rate of organism 'b' in mono-culture condition in 'D', $A_b$ is the abundance of organism 'b' in the gut microbiota of the subject requiring personalization, $T_b$ is the M-types of organism 'b', wherein the abundance of the organism 'b' in the gut microbiota of the subject requiring personalization is capped by an abundance factor to avoid over-estimating an influence including the sustainability or the net-effect due to large variation in the abundance of the microbe comprising the gut microbiota of the subject requiring personalization;

select an efficacious probiotic organism based on at least one of the net-effect and the sustainability;

design a personalized probiotic intervention regimen in the form of a probiotics treatment to the subject based on the selected efficacious probiotic organism; and administer the efficacious probiotic organism to the subject to improve the gut microbiota, wherein a dosage requirement for the efficacious probiotic organism is least when the efficacious probiotic organism is selected with a highest sustainability and the net-effect to deliver optimal therapeutic outcome, wherein when a probiotic organism with both the highest sustainability and the net-effect is not identified, then a probiotic organism with the highest sustainability and moderately high net-effect is selected and administration or the dosage requirement of the probiotic organism is the least of all available probiotic therapy options, wherein when the probiotic organism with a highest net-effect and a moderately high sustainability is selected, then the effect of the probiotic intervention is optimal of all the available probiotic therapy options, and the dosage requirement of the probiotic organism is more frequent or higher dosage, and wherein the system is implemented for the probiotics treatment to the subject requiring personalization based on the efficacious probiotic organism to improve the gut microbiota.

9. The system of claim 8, wherein the set of metabolic constraints is defined by (a) identifying and quantifying one or more nutrients constituting the one or more dietary preferences of the subject requiring personalization, and (b) converting the one or more quantified nutrients into the set of metabolic constraints, and wherein the set of metabolic constraints is defined based on the common diets of at least one of a region and an ethnic population to which the subject belongs to, if the one or more dietary preferences of the subject requiring personalization is not available and the information regarding the one or more dietary preferences of the subject is obtained from the database.

10. The system of claim 8, wherein the microbial abundance is determined by determining the microbial abundance of a predefined set of microbes using multiple DNA characterization techniques including Next Generation Sequencing protocols (NGS), a multiplex quantitative Polymerase Chain Reaction (qPCR) technique, nucleic acid hybridization techniques and the like, and wherein the microbial abundance of each microbe constituting the gut microbiota of the subject is defined as at least one of the mean microbial abundance of each microbe constituting the gut microbiota of an ethnic group and one or more lifestyle habits to which the subject belongs to, using information from the database, if the taxonomic profile associated with the test biological sample is not available.

11. The system of claim 8, wherein the microbial abundance is determined by determining the microbial abundance of a predefined set of microbes using multiple DNA characterization techniques including Next Generation Sequencing protocols (NGS), a multiplex quantitative Polymerase Chain Reaction (qPCR) technique, nucleic acid hybridization techniques and the like, and wherein the microbial abundance of each microbe constituting the gut microbiota of the subject is defined as at least one of the mean microbial abundance of each microbe constituting the gut microbiota of an ethnic group and one or more lifestyle habits to which the subject belongs to, using information from the database, if the taxonomic profile associated with the test biological sample is not available.

12. The system of claim 8, wherein a list of probiotic organisms stored in the database is used, if at least one probiotic organisms dataset is not available.

13. The system of claim 8, wherein the genome scale metabolic models of microbes comprising the gut microbiota and the plurality of probiotic organisms available in the database is used.

14. The system of claim 8, wherein the information regarding M-type of the microbes constituting the gut microbiota of the subject requiring personalization is obtained from at least one of database, a public repository and a literature survey.

15. One or more non-transitory machine-readable information storage mediums comprising one or more instructions which when executed by one or more hardware processors cause:

receiving an information specific to one or more dietary preferences of a subject requiring personalization from one or more communication media;

defining a set of metabolic constraints for the one or more dietary preferences of the subject requiring personalization, wherein the set of metabolic constraints are used for one or more metabolic simulations;

receiving a test biological sample of the subject requiring personalization from the one or more communication media;

extracting DNA (Deoxyribonucleic Acid) from the test biological sample, using a DNA extraction technique;

determining a microbial abundance of each microbe present in the test biological sample, from the microbial DNA which comprises a gut microbiota, using a set of probes specific to each of the microbes from stretches of DNA sequences sequenced from the microbial DNA extracted from the test biological sample, to obtain a microbial taxonomic profile associated with the test biological sample, wherein the microbial taxonomic profile associated with the test biological sample comprises microbial abundance of each of the microbes corresponding to a set of microbial DNA sequences present in the test biological sample;

obtaining an information specific to a plurality of probiotic organisms from at least one probiotic organisms dataset to evaluate the efficacy of the plurality of probiotic organisms;

creating a plurality of genome scale metabolic models of each of a plurality of microbes comprised in the gut microbiota of the subject and each of the plurality of probiotic organisms whose efficacy are be evaluated;

assigning M-type to the plurality of microbes comprised in the gut microbiota as T=+1 for at least one of beneficial microbes and commensal microbes and T=−1 for at least one of pathogenic microbes and opportunistic microbes;

performing the one or more metabolic simulations to ascertain a mono-culture growth of each of the plurality of microbes comprising the gut microbiota and each of the organism comprised in the plurality of probiotic organisms by using the defined set of metabolic constraints for simulating the one or more dietary preferences of the subject;

performing the one or more metabolic simulations to ascertain a co-culture growth of every pair of the plurality of microbes comprised in the gut microbiota and each of the organism comprised in the plurality of probiotic organisms by using the defined set of metabolic constraints for simulating the one or more dietary preferences of the subject, wherein the one or more metabolic simulations include in-silico metabolic simulations including a flux balance simulation for simulating metabolic behaviour of an organism under the set of metabolic constraints and simulating an effect of probiotic interventions on a plurality of gut microbiota compositions and the one or more dietary preferences of the subject;

computing sustainability of each of the organism comprised in the plurality of probiotic organisms for evaluating the capability of each of the organism comprised in the plurality of probiotic organisms to proliferate within the gut, wherein the sustainability is defined as:

$$D_{[Sustainability]_a} = \sum\left(\frac{G_a^p}{G_a^s}\right) * A_b;$$

where 'D' is the set of metabolic constraints defining the one or more dietary preferences of the subject requiring personalization, 'a' is the probiotic organism, 'b' represents each of the microbes constituting the gut microbiota of the subject requiring personalization, $A_b$ is the abundance of organism 'b' the gut microbiota of the subject requiring personalization, $$G_a^p$$

is the growth rate of organism 'a' in co-growth condition with each of the microbes constituting the gut microbiota of the subject requiring personalization 'b' in 'D', $$G_a^s$$

is the growth rate of organism 'a' in mono-culture condition in 'D';

computing net-effect of each of the organism comprised in the plurality of probiotic organisms for quantifying an overall influence of the plurality of probiotic organisms as a score by summating a plurality of positive influences and a plurality of negative influences on each of the microbes comprised in the gut microbiota, wherein the plurality of positive influences comprise the growth and proliferation of at least one of the beneficial microbes and at least one of the commensal microbes and the plurality of negative influences comprises the growth and proliferation of at least one of the pathogenic microbes and at least one of the opportunistic microbes, wherein the net-effect reflects a net change in growth rates of the plurality of microbes in the gut microbiota as a consequence of administering a probiotic, and wherein the net-effect is defined as:

$$D_{[Net-effect]_a} = \sum\left(\frac{G_b^p}{G_b^s}\right) * A_b * T_b;$$

where 'D' is the set of metabolic constraints defining the one or more dietary preference of the subject requiring personalization, 'b' represents each of the microbes constituting the gut microbiota of the subject requiring personalization, $$G_b^p$$

is the growth rate of organism 'b' in co-cultured condition with the probiotic organism 'a' in 'D', $$G_b^s$$

is the growth rate of organism 'b' in mono-culture condition in 'D', $A_b$ is the abundance of organism 'b' in the gut microbiota of the subject requiring personalization, $T_b$ is the M-types of organism 'b', wherein the abundance of the organism 'b' in the gut microbiota of the subject requiring personalization is capped by an abundance factor to avoid over-estimating an influence including the sustainability or the net-effect due to large variation in the abundance of the microbe comprising the gut microbiota of the subject requiring personalization;

selecting an efficacious probiotic organism based on at least one of the net-effect and the sustainability;

designing a personalized probiotic intervention regimen in the form of a probiotics treatment to the subject based on the selected efficacious probiotic organism; and administering the efficacious probiotic organism to the subject to improve the gut microbiota, wherein a dosage requirement for the efficacious probiotic organism is least when the efficacious probiotic organism is selected with a highest sustainability and the net-effect to deliver optimal therapeutic outcome, wherein when a probiotic organism with both the highest sustainability and the net-effect is not identified, then a probiotic organism with the highest sustainability and moderately high net-effect is selected and administration or the dosage requirement of the probiotic organism is the least of all available probiotic therapy options, wherein when the probiotic organism with a highest net-effect and a moderately high sustainability is selected, then the effect of the probiotic intervention is optimal of all the available probiotic therapy options, and the dosage requirement of the probiotic organism is more frequent or higher dosage, and wherein a method is implemented for the probiotics treatment to the subject requiring personalization based on the efficacious probiotic organism to improve the gut microbiota.

16. The one or more non-transitory machine-readable information storage mediums of claim 15, wherein defining the set of metabolic constraints includes (a) identifying and quantifying one or more nutrients constituting the one or more dietary preferences of the subject requiring personalization, and (b) converting the one or more quantified nutrients into the set of metabolic constraints, and wherein the set of metabolic constraints is defined based on the common diets of at least one of a region and an ethnic population to which the subject belongs to, if the one or more dietary preferences of the subject requiring personalization is not available and the information regarding the one or more dietary preferences of the subject is obtained from the database.

17. The one or more non-transitory machine-readable information storage mediums of claim 15, wherein the step of determining the microbial abundance comprises determining the microbial abundance of a predefined set of microbes using multiple DNA characterization techniques including Next Generation Sequencing protocols (NGS), a multiplex quantitative Polymerase Chain Reaction (qPCR) technique, nucleic acid hybridization techniques and the like, and wherein the microbial abundance of each microbe constituting the gut microbiota of the subject is defined as at least one of the mean microbial abundance of each microbe constituting the gut microbiota of an ethnic group and one or more lifestyle habits to which the subject belongs to, using information from the database, if the taxonomic profile associated with the test biological sample is not available.

18. The one or more non-transitory machine-readable information storage mediums of claim 15, wherein a list of probiotic organisms stored in the database is used, if at least one probiotic organisms dataset is not available, wherein the genome scale metabolic models of microbes comprising the gut microbiota and the plurality of probiotic organisms available in the database is used, and wherein the information regarding M-type of the microbes constituting the gut microbiota of the subject requiring personalization is obtained from at least one of database, a public repository, and a literature survey.

* * * * *